US006479512B1

(12) United States Patent
Fraley et al.

(10) Patent No.: US 6,479,512 B1
(45) Date of Patent: Nov. 12, 2002

(54) TYROSINE KINASE INHIBITORS

(75) Inventors: Mark E. Fraley, North Wales; Scott R. Hambaugh, Norristown; Randall W. Hungate, Lansdale, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/690,602

(22) Filed: Oct. 17, 2000

Related U.S. Application Data

(60) Provisional application No. 60/160,362, filed on Oct. 19, 1999.

(51) Int. Cl.[7] ...................... A61K 31/47; C07D 215/16; C07D 215/20
(52) U.S. Cl. ........................ 514/312; 514/313; 514/314; 546/153; 546/157
(58) Field of Search ................................ 546/153, 157; 514/312, 313, 314

(56) References Cited

FOREIGN PATENT DOCUMENTS

| WO | WO00/09495 | | 2/2000 |
|----|------------|---|--------|
| WO | 2001028993 | * | 4/2001 |

OTHER PUBLICATIONS

CA 128:2030, abstract of Ukrainets, chem Heterocycl Comp (N.Y.) 1997, 33(5), 600–604.*
Oncogene, vol. 5, pp. 519–524 (1990), by M. Shibuya, et al.
FEBS Letters, vol. 473, pp. 161–164 (2000), by M. Nakagawa, et al.
Stem Cells, vol. 12, pp. 1–6 (1994), by T. R. Burke, Jr.
Molecular Cell, vol. 4, pp. 915–924 (1999), by B. Elceiri, et al.
Oncogene, vol. 6, pp. 1677–1683 (1991), by B. Terman, et al.
Nature Medicine, vol. 5, No. 6, pp. 623–628 (1999), by H. Gerber, et al.
Nature Biotech, vol. 17, pp. 963–968 (1999), by V. Brower.
J. of Clin. Investigation, vol. 104, No. 11, pp. 1613–1620 (1999), by N. van Bruggen, et al.
Drug News Perspect, vol. 11, No. 5, pp. 265–270 (1998), by D. A. Greenberg.
Nature, vol. 407, pp. 242–248 (2000), by G. Yancopoulos, et al.
Nature, vol. 407, pp. 249–257 (2000), by P. Carmeliet, et al.
Platelets, vol. 10, pp. 285–292 (1999), by A. Amirkhosravi, et al.
Endocrinology, Abstract, vol. 141, No. 5, pp. 1667–1674 (2000), by M. Deckers, et al.
Tetrahedron Letters, vol. 36, No. 42, pp. 7747–7748 (1995), by Ukrainets, et al.

* cited by examiner

*Primary Examiner*—D. Margaret Seaman
(74) *Attorney, Agent, or Firm*—Dianne Brown; Mark R. Daniel

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

31 Claims, No Drawings

TYROSINE KINASE INHIBITORS

RELATED APPLICATIONS

This application claims priority under 35 U.S.C. § 119(e) from U.S. Provisional Application No. 60/160,362 filed Oct. 19$^{th}$, 1999.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanism of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene*, 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperinmmune responses.

Several receptor-type tyrosine kinases, and the growth factors that bind thereto, have been suggested to play a role in angiogenesis, although some may promote angiogenesis indirectly (Mustonen and Alitalo, *J. Cell Biol.* 129:895–898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11–15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, *Cytokine & Growth Factor Reviews* 7:259–270, 1996). VEGF binds the high affinity membrane-spanning tyrosine kinase receptor KDR and the related fins-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual eneration culminating in blindness. Ocular VEGF MRNA and protein are elevated by conditions such as retinal vein occlusion in primates and decreased pO$_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Accordingly, the identification of small compounds which specifically inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof:

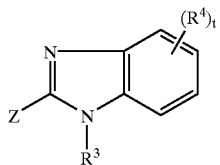

I

DETAILED DESCRIPTION OF THE INVENTION

The compounds of this invention are useful in the inhibition of kinases and are illustrated by a compound of Formula I:

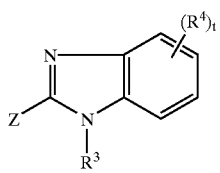

I or a pharmaceutically acceptable salt or stereoisomer thereof, wherein

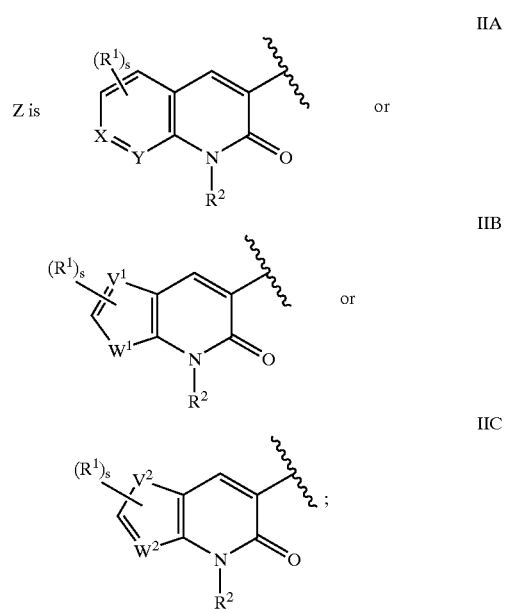

$W^1$ is S, O, or N—R;
$V^1$ is N or C;
$W^2$ is N or C;
$V^2$ is S, O, or N—R;
a is 0 or 1;
b is 0 or 1;
s is 1 or 2;
t is 1, 2, or 3;
X=Y is C=N, N=C, or C=C;
R is H or $C_1$–$C_6$ alkyl;
$R^1$ is selected from:
  1) H,
  2) $(C=O)_a O_b C_1$–$C_{10}$ alkyl,
  3) $(C=O)_a O_b$ aryl,
  4) $(C=O)_a O_b C_2$–$C_{10}$ alkenyl,
  5) $(C=O)_a O_b C_2$–$C_{10}$ alkynyl,
  6) $CO_2 H$,
  7) halo,
  8) OH,
  9) $O_b C_1$–$C_6$ perfluoroalkyl,
  10) $(C=O)_a NR^7 R^8$,
  11) CN,
  12) $(C=O)_a O_b C_3$–$C_8$ cycloalkyl, and
  13) $(C=O)_a O_b$ heterocyclyl,
said alkyl, aryl, alkenyl, alkynyl, cycloalkyl, and heterocyclyl is optionally substituted with one or more substituents selected from $R^6$;
$R^2$ and $R^3$ are independently selected from:
  1) H,
  2) $(C=O)O_a C_1$–$C_6$ alkyl,
  3) $(C=O)O_a$ aryl,
  4) $C_1$–$C_6$ alkyl,
  5) $SO_2 R^a$, and
  6) aryl;
$R^4$ is selected from:
  1) H, provided that Z is not IIA when X=Y is C=C,
  2) $(C=O)_a O_b C_1$–$C_{10}$ alkyl,
  3) $(C=O)_a O_b$ aryl,
  4) $(C=O)_a O_b C_2$–$C_{10}$ alkenyl,
  5) $(C=O)_a O_b C_2$–$C_{10}$ alkynyl, 6) CO$_2$H,
7) halo,
8) OH,
9) O$_b$C$_1$–C$_6$ perfluoroalkyl,
10) (C=O)$_a$NR$^7$R$^8$,
11) CN,
12) (C=O)$_a$O$_b$C$_3$–C$_8$ cycloalkyl, and
13) (C=O)$_a$O$_b$heterocyclyl, said alkyl, aryl, alkenyl, alkynyl, cycloalkyl, and heterocyclyl is optionally substituted with one or more substituents selected from R$^6$;

R$^6$ is:
1) (C=O)$_a$O$_b$C$_1$–C$_{10}$ alkyl,
2) (C=O)$_a$O$_b$aryl,
3) C$_2$–C$_{10}$ alkenyl,
4) C$_2$–C$_{10}$ alkynyl,
5) (C=O)$_a$O$_b$ heterocyclyl,
6) CO$_2$H,
7) halo,
8) CN,
9) OH,
10) O$_b$C$_1$–C$_6$ perfluoroalkyl,
11) O$_a$(C=O)$_b$NR$^7$R$^8$,
12) oxo,
13) CHO,
14) (N=O)R$^7$R$^8$, and
15) (C=O)$_a$O$_b$C$_3$–C$_8$ cycloalkyl, said alkyl, aryl, alkenyl, alkynyl, heterocyclyl, and cycloalkyl optionally substituted with one or more substituents selcted from R$^{6a}$;

R$^{6a}$ is selected from:
1) (C=O)$_r$O$_s$(C$_1$–C$_{10}$)alkyl, wherein r and s are independently 0 or 1,
2) O$_r$(C$_1$–C$_3$)perfluoroalkyl, wherein r is 0 or 1,
3) (C$_0$–C$_6$)alkylene-S(O)$_m$R$^a$, wherein m is 0, 1, or 2,
4) oxo,
5) OH,
6) halo,
7) CN,
8) (C$_{214}$ $_{C10}$)alkenyl,
9) (C$_2$–C$_{10}$)alkynyl,
10) (C$_3$–C$_6$)cycloalkyl,
11) (C$_0$–C$_6$)alkylene-aryl,
12) (C$_0$–C$_6$)alkylene-heterocyclyl,
13) (C$_0$–C$_6$)alkylene-N(R$^b$)$_2$,
14) C(O)R$^a$,
15) (C$_0$–C$_6$)alkylene-CO$_2$R$^a$,
16) C(O)H, and
17) (C$_0$–C$_6$)alkylene-CO$_2$H, said alkyl, alkenyl, alkynyl, cycloalkyl, aryl, and heterocyclyl is optionally substituted with up to three substituents selected from R$^b$, OH, (C$_1$–C$_6$)alkoxy, halogen, CO$_2$H, CN, O(C=O)C$_1$–C$_6$ alkyl, oxo, and N(R$^b$)$_2$;

R$^7$ and R$^8$ are independently selected from:
1) H,
2) (C=O)O$_b$C$_1$–C$_{10}$ alkyl,
3) (C=O)O$_b$C$_3$–C$_8$ cycloalkyl,
4) (C=O)O$_b$aryl,
5) (C=O)O$_b$heterocyclyl,
6) C$_1$–C$_{10}$ alkyl,
7) aryl,
8) C$_2$–C$_{10}$ alkenyl,
9) C$_2$–C$_{10}$ alkynyl,
10) heterocyclyl,
11) C$_3$–C$_8$ cycloalkyl,
12) SO$_2$R$^a$,
13) (C=O)NR$^b{}_2$, said alkyl, cycloalkyl, aryl, heterocylyl, alkenyl, and alkynyl is optionally substituted with one or more substituents selected from R$^{6a}$, or R$^7$ and R$^8$ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocylcic or bicyclic heterocycle optionally substituted with one or more substituents selected from R$^{6a}$;

R$^a$ is (C$_1$–C$_6$)alkyl, (C$_3$–C$_6$)cycloalkyl, aryl, or heterocyclyl; and R$^b$ is H, (C$_1$–C$_6$)alkyl, aryl, heterocyclyl, (C$_3$–C$_6$) cycloalkyl, (C=O)OC$_1$–C$_6$ alkyl, (C=O)C$_1$–C$_6$ alkyl or S(O)$_2$R$^a$.

A second embodiment of the present invention exemplified by a compound of Formula I wherein W$^1$ is S or N—R and V$^2$ is S or N—R.

Another embodiment is a compound as described immediately above, wherein R$^1$ is selected from:
1) H,
2) (C=O)$_a$O$_b$C$_1$–C$_6$ alkyl,
3) (C=O)$_a$O$_b$C$_2$–C$_6$ alkenyl,
4) (C=O)$_a$O$_b$C$_2$–C$_6$ alkynyl,
5) CO$_2$H,
6) halo,
7) OH,
8) O$_b$C$_1$–C$_3$ perfluoroalkyl,
9) CN, and
10) (C=O)$_a$O$_b$C$_3$–C$_6$ cycloalkyl;

R$^2$ and R$^3$ are independently selected from:
1) H,
2) (C=O)O$_a$C$_1$–C$_6$ alkyl,
3) C$_1$–C$_6$ alkyl, and
4) SO$_2$R$^a$;

R$^4$ is selected from:
1) H, provided that Z is not IIA when X=Y is C=C,
2) (C=O)$_a$O$_b$C$_1$–C$_6$ alkyl,
3) (C=O)$_a$O$_b$aryl,
4) (C=O)$_a$O$_b$C$_2$–C$_6$ alkenyl,
5) (C=O)$_a$O$_b$C$_2$–C$_6$ alkynyl,
6) CO$_2$H,
7) halo,
8) OH,
9) O$_b$C$_1$–$_3$ perfluoroalkyl,
10) (C=O)$_a$NR$^7$R$^8$,
11) CN,
12) (C=O)$_a$O$_b$C$_3$–C$_6$ cycloalkyl, and
13) (C=O)$_a$O$_b$heterocyclyl, said alkyl, aryl, alkenyl, alkynyl, cycloalkyl, and heterocyclyl is optionally substituted with one or more substituents selected from R$^6$;

R$^6$ is:
1) (C=O)$_a$O$_b$C$_{1-6}$ alkyl,
2) (C=O)$_a$O$_b$aryl,
3) C$_2$–C$_6$ alkenyl,
4) C$_2$–C$_6$ alkynyl,
5) (C=O)$_a$O$_b$heterocyclyl,
6) CO$_2$H,
7) halo,
8) CN,
9) OH,
10) O$_b$C$_1$–C$_3$ perfluoroalkyl, or 11) $O_a(C=O)_bNR^7R^8$,
12) oxo,
13) CHO,
14) $(N=O)R^7R^8$, and
15) $(C=O)_aO_bC_3-C_6$ cycloalkyl, said alkyl, aryl, alkenyl, alkynyl, heterocyclyl, and cycloalkyl optionally substituted with one or more substituents selected from $R^{6a}$;

$R^{6a}$ is selected from:
1) $(C=O)_rO_s(C_1-C_6)$alkyl, wherein r and s are independently 0 or 1,
2) $O_r(C_1-C_3)$perfluoroalkyl, wherein r is 0 or 1,
3) $(C_0-C_6)$alkylene-$S(O)_mR^a$, wherein m is 0, 1, or 2,
4) oxo,
5) OH,
6) halo,
7) CN,
8) $(C_2-C_{10})$alkenyl,
9) $(C_2-C_{10})$alkynyl,
10) $(C_3-C_6)$cycloalkyl,
11) $(C_0-C_6)$alkylene-aryl,
12) $(C_0-C_6)$alkylene-heterocyclyl,
13) $(C_0-C_6)$alkylene-$N(R^b)_2$,
14) $C(O)R^a$,
15) $(C_0-C_6)$alkylene-$CO_2R^a$,
16) C(O)H, and
17) $(C_0-C_6)$alkylene-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, and $N(R^b)_2$;

$R^7$ and $R^8$ are independently selected from:
1) H,
2) $(C=O)O_bC_1-C_6$ alkyl,
3) $(C=O)O_bC_3-C_6$ cycloalkyl,
4) $(C=O)O_b$aryl,
5) $(C=O)O_b$heterocyclyl,
6) $C_1-C_6$ alkyl,
7) aryl,
8) $C_2-C_6$ alkenyl,
9) $C_2-C_6$ alkynyl,
10) heterocyclyl,
11) $C_3-C_6$ cycloalkyl,
12) $SO_2R^a$,
13) $(C=O)NR^b_2$, said alkyl, cycloalkyl, aryl, heterocylyl, alkenyl, and alkynyl is optionally substituted with one or more substituents selected from $R^{6a}$, or $R^7$ and $R^8$ can be taken together with the nitrogen to which they are attached to form a monocyclic, 5–7 membered heterocycle and optionally containing, in addition to the nitrogen, one additional heteroatom selected from N, O and S, said heterocycle optionally substituted with one or more substituents selected from $R^{6a}$.

And yet another embodiment of the invention is the compound described above, wherein

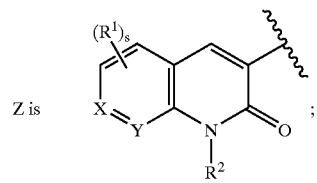

Z is

IIA

X=Y is C=C;
R is H or $C_1-C_6$ alkyl;
$R^1$ is selected from:
1) H,
2) $(C=O)_aO_bC_1-C_6$ alkyl,
3) $(C=O)_aO_bC_2-C_6$ alkenyl,
4) $(C=O)_aO_bC_2-C_6$ alkynyl,
5) $CO_2H$,
6) halo,
7) OH,
8) $O_bC_1-C_3$ perfluoroalkyl,
9) CN, and
10) $(C=O)_aO_bC_3-C_8$ cycloalkyl;

$R^2$ and $R^3$ are independently selected from:
1) H,
2) $(C=O)O_aC_1-C_6$ alkyl,
3) $C_1-C_6$ alkyl, and
4) $SO_2R^a$;

$R^4$ is selected from:
1) $(C=O)_aO_bC_1-C_{10}$ alkyl,
2) $(C=O)_aO_b$aryl,
3) $(C=O)_aO_bC_2-C_{10}$ alkenyl,
4) $(C=O)_aO_bC_2-C_{10}$ alkynyl,
5) $CO_2H$,
6) halo,
7) OH,
8) $O_bC_1-C_6$ perfluoroalkyl,
9) $(C=O)_aNR^7R^8$,
10) CN,
11) $(C=O)_aO_bC_3-C_8$ cycloalkyl, and
12) $(C=O)_aO_b$heterocyclyl, said alkyl, aryl, alkenyl, alkynyl, cycloalkyl, and heterocyclyl is optionally substituted with one or more substituents selected from $R^6$;

$R^7$ and $R^8$ are independently selected from:
1) H,
2) $(C=O)O_bC_1-C_{10}$ alkyl,
3) $(C=O)O_bC_3-C_8$ cycloalkyl,
4) $(C=O)O_b$aryl,
5) $(C=O)O_b$heterocyclyl,
6) $C_1-C_{10}$ alkyl,
7) aryl,
8) $C_2-C_{10}$ alkenyl,
9) $C_2-C_{10}$ alkynyl,
10) heterocyclyl,
11) $C_3-C_8$ cycloalkyl,
12) $SO_2R^a$,
13) $(C=O)NR^b_2$, said alkyl, cycloalkyl, aryl, heterocylyl, alkenyl, and alkynyl is optionally substituted with one or more substituents selected from $R^{6a}$, or $R^7$ and $R^8$ can be taken together with the nitrogen to which they are attached to form a monocyclic 5–7 memebered heterocycle and optionally containing, in addition to the nitrogen, one additional heteroatom selected from N, O and S, said heterocycle optionally substituted with one or more substituents selected from R6a.

A further embodiment is the compound described above, wherein s is 1;

t is 1 or 2;

R is H or $C_1$–$C_6$ alkyl;

$R^1$ is selected from:
1) H,
2) $OC_1$–$C_6$ alkyl,
3) $C_1$–$C_6$ alkyl,
4) halo,
5) OH,
6) $OC_1$–$C_3$ perfluoroalkyl,
7) $OC_1$–$C_3$ perfluoroalkyl,
8) $OC_3$–$C_6$ cycloalkyl, and
9) $C_3$–$C_6$ cycloalkyl;

$R^2$ and $R^3$ are H;

$R^4$ is selected from:
1) $OC_1$–$C_6$ alkyleneNR$^7$R$^8$,
2) $(C=O)_a C_0$–$C_6$ alkyl, said alkyl optionally substituted with OH, $CO_2H$, or $OC_1$–$C_6$ alkyl,
3) $OC_0$–$C_6$ alkylene-heterocyclyl, optionally substituted with one to three substituents selected from $R^{6a}$,
4) $C_0$–$C_6$ alkyleneNR$^7$R$^8$,
5) $(C=O)NR^7R^8$, and
6) $OC_1$–$C_3$ alkylene-$(C=O)NR^7R^8$.

A preferred embodiment is a compound selected from:

3-[5-(2-piperidin-1-yl-ethoxy)-benzimidazol-2-yl]-quinolin-2-one;

3-[5-(2-piperidin-1-yl-propoxy)-benzimidazol-2-yl]-quinolin-2-one;

2-(2-oxo-1,2-dihydro-quinolin-3-yl)-benzoimidazole-5-carboxylic acid (2-pyrrolidin-1-yl-ethyl)-amide;

3-[5-(1-piperazinylcarbonyl)-1H-benzimidazol-2-yl]-2 (1H)-quinolinone; and

3-{5-[(4-amnino-1-piperidinyl)carbonyl]-1H-benzimidazol-2-yl}-2(1H)-quinoline, or a pharmaceutically acceptable salt or stereoisomer thereof Also included within the scope of the present invention is a pharmaceutical composition which is comprised of a compound of Formula I as described above and a pharmaceutically acceptable carrier. The present invention also encompasses a method of treating or preventing cancer in a mammal in need of such treatment which is comprised of administering to said mammal a therapeutically effective amount of a compound of Formula I. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, gioblastomas and breast carcinoma.

Also included is a method of treating or preventing a disease in which angiogenesis is implicated, which is comprised of administering to a mammal in need of such treatment a therapeutically effective amount of a compound of Formula I. Such a disease in which angiogenesis is implicated is ocular diseases such as retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formula 1. Examples of such inflammatory diseases are rheumatoid arthritis, psoriasis, contact dermatitis, delayed hypersensitivity reactions, and the like.

Also included is a method of treating or preventing a tyrosine kinase-dependent disease or condition in a mammal which comprises administering to a mammalian patient in need of such treatment a therapeutically effective amount of a compound of Formula I. The therapeutic amount varies according to the specific disease and is discemable to the skilled artisan without undue experimentation.

A method of treating or preventing retinal vascularization which is comprised of administering to a mammal in need of such treatment a therapeutically effective amount of compound of Formula 1 is also encompassed by the present invention. Methods of treating or preventing ocular diseases, such as diabetic retinopathy and age-related macular degeneration, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets.

The invention also contemplates the use of the instantly claimed compounds in combination with a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer which comprises administering a therapeutically effective amount of a compound of Formula 1 in combination with radiation therapy and/or in combination with a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formula 1 in combination with paclitaxel or trastuzumab.

Also within the scope of the invention is a method of reducing or preventing tissue damage following a cerebral ischemic event which comprises administering a therapeutically effective amount of a compound of Formula I.

These and other aspects of the invention will be apparent from the teachings contained herein.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like).

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

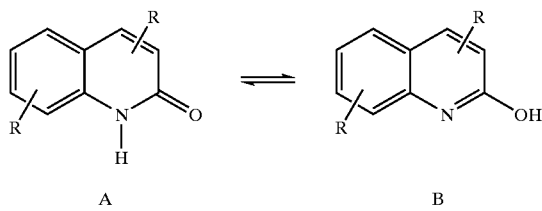

A                                      B

When any variable (e.g. $R^4$, $R^6$, $R^{6a}$, etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear or branched arrangement. For example, "$C_1$–$C_{10}$ alkyl" specifically includes methyl, ethyl, n-propyl, i-propyl, n-butyl, t-butyl, i-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" inlcudes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$–$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$–$C_6$) alkylene-aryl. If aryl is taken to be phenyl, this definition would include phenyl itself as well as —$CH_2$Ph, —$CH_2CH_2$Ph, $CH(CH_3)CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo. The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The alkyl, alkenyl, alkynyl, cycloalkyl, aryl, heteroaryl and heterocyclyl substituents may be unsubstituted or unsubstituted, unless specifically defined otherwise. For example, a $(C_1-C_6)$alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C=O)CH$_2$CH(OH)CH$_3$, —(C=O)OH, —CH$_2$(OH)CH$_2$CH(O), and so on.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

In certain instances, $R^7$ and $R^8$ are defined such that they can be taken together with the nitrogen to which they are attached to form a monocyclic or bicyclic heterocycle with 5–7 members in each ring and optionally containing, in addition to the nitrogen, one or two additional heteroatoms selected from N, O and S, said heterocycle optionally substituted with one or more substituents selected from R6a. Examples of the heterocycles that can thus be formed include, but are not limited to the following, keeping in mind that the heterocycle is optionally substituted with one or more substituents chosen from $R^{6a}$:

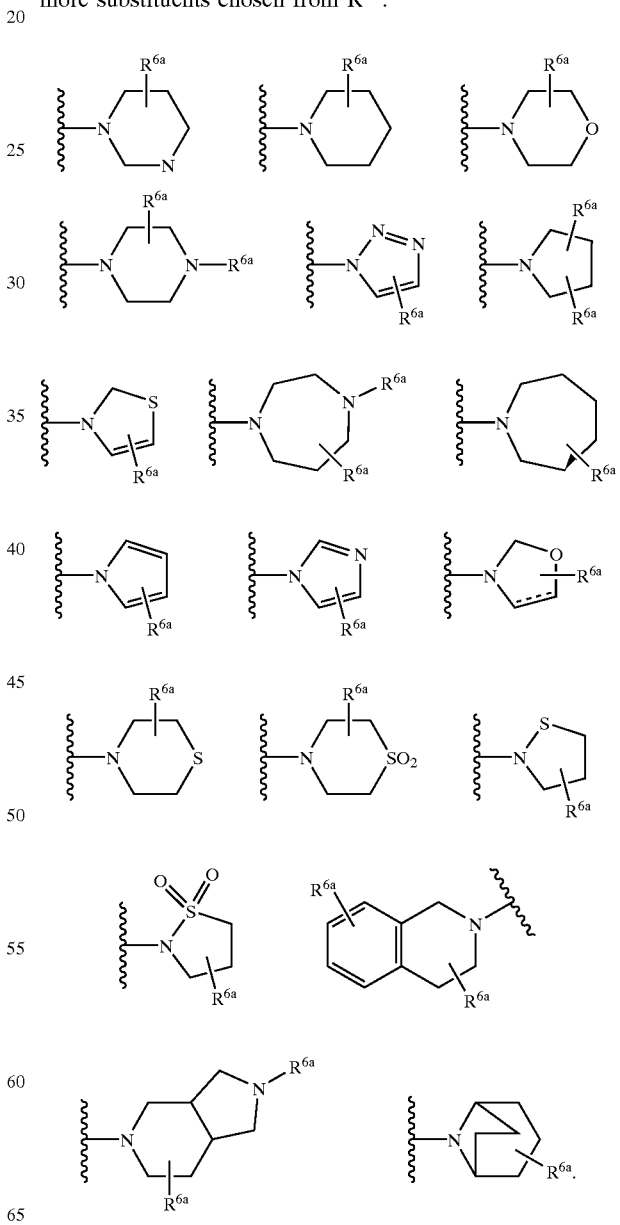

Preferably $R^1$ is H, halo, $OC_1$–$C_6$ alkyl, and $C_1$–$C_6$ alkyl. More preferably $R^1$ is H. Also prefered is the definition of $R^2$ and $R^3$ as H. The preferred heterocyclyl substituents are those shown immediately above plus pyrdidine, pyrimidine, pyrazine, pyridazine, tetramethylenesulfone, butyrolactone, tetrahydrofuran, furan, indole, and thiophene. Preferably t is 1 and $R^4$ is displaced at the 5-position of the benzoimidazole, according to the following numbering scheme:

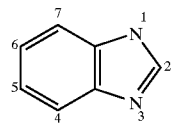

Preferably $R^4$ is defined as $OC_1$–$C_6$ alkyleneNR$^7$R$^8$; (C=O)$_a$C$_0$–C$_6$ alkyl, wherein the alkyl is optionally substituted with OH, $CO_2H$, or $OC_1$–$C_6$ alkyl; $OC_0$–$C_6$ alkylene-heterocyclyl, optionally substituted with one to three substituents selected from $R^{6a}$; $C_0$–$C_6$ alkyleneNR$^7$R$^8$; (C=O)NR$^7$R$^8$; or $OC_1$–$C_3$ alkylene-(C=O)NR$^7$R$^8$. Most preferably $R^4$ is $C_1$–$C_3$ alkyleneNR$^7$R$^8$. Preferably $R^7$ and $R^8$ are defined such that they are be taken together with the nitrogen to which they are attached to form a monocyclic 5–7 membered heterocycle and optionally containing, in addition to the nitrogen, one or two additional heteroatoms selected from N, O and S, and said heterocycle optionally substituted with one or more substituents selected from $R^{6a}$.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

SCHEMES

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

The compounds of this invention may be prepared by employing reactions as shown in the schemes below in addition to other standard manipulations as are known in the literature or exemplified in the experimental procedures. These schemes, therefore, are not limited by the compounds listed nor by any particular substituents employed for illustrative purposes. Substituent numbering as shown in the Schemes do not necessarily correlate to that used in the claims.

Schemes A–D below exemplify some of the synthetic routes available to prepare the compounds disclosed. Schemes A–C illustrate various approaches to the formation of the benzoimidazole portion of the instantr compounds. Scheme D illustrates the synthesis of the thienopyridinone or oxazole counterparts.

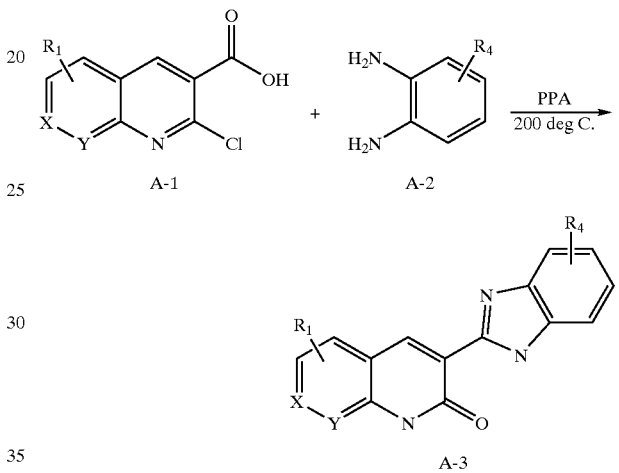

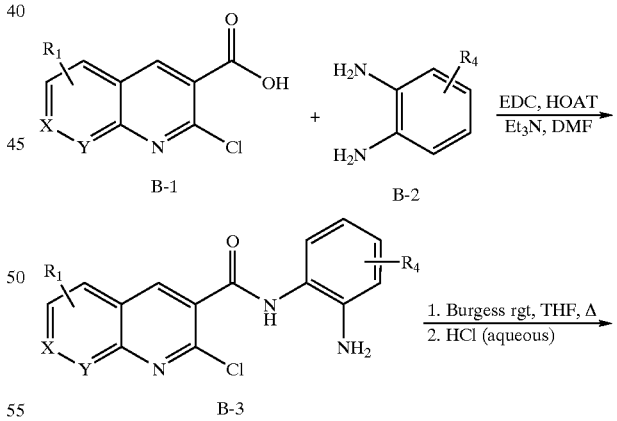

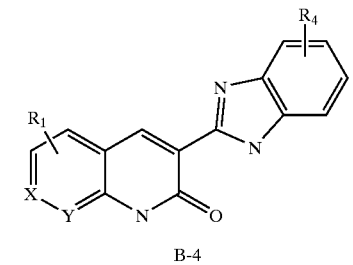

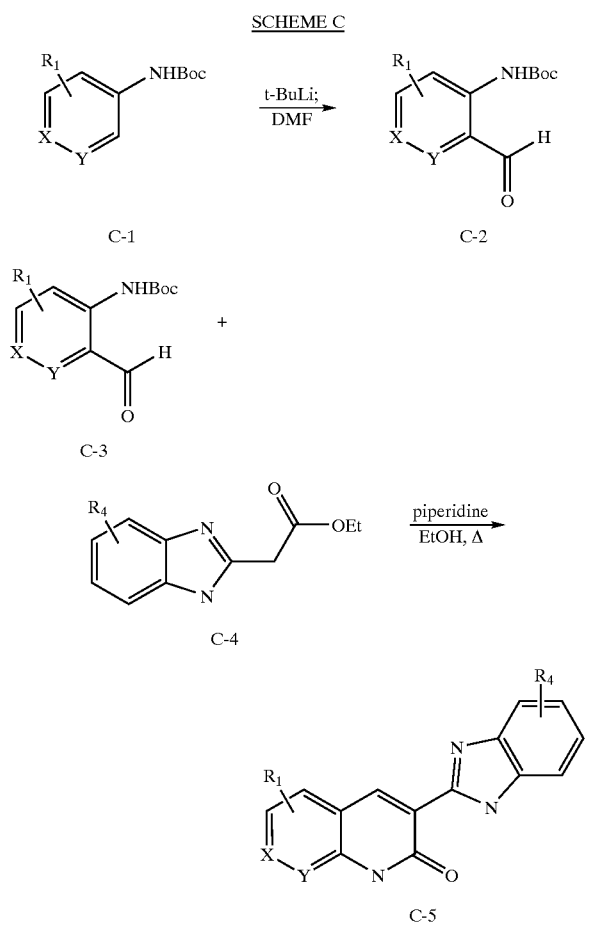

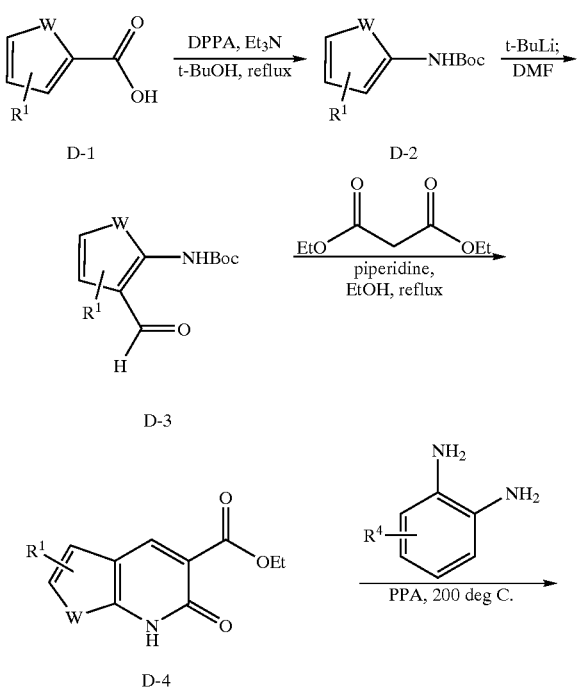

UTILITY

The instant compounds are useful as pharmaceutical agents for mammals, especially for humans, in the treatment of tyrosine kinase dependent diseases. Such diseases include the proliferation of tumor cells, the pathologic neovascularization (or angiogenesis) that supports solid tumor growth, ocular neovascularization (diabetic retinopathy, age-related macular degeneration, and the like) and inflammation (psoriasis, rheumatoid arthritis, and the like).

The compounds of the instant invention may be administered to patients for use in the treatment of cancer. The instant compounds inhibit tumor angiogenesis, thereby affecting the growth of tumors (J. Rak et al. *Cancer Research*, 55:4575–4580, 1995). The anti-angiogenesis properties of the instant compounds are also useful in the treatment of certain forms of blindness related to retinal vascularization.

The disclosed compounds are also useful in the treatment of certain bone-related pathologies, such as osteosarcoma, osteoarthritis, and rickets, also known as oncogenic osteomalacia. (Hasegawa et al., Skeletal Radiol., 28, pp.41–45, 1999; Gerber et al., Nature Medicine, Vol. 5, No. 6, pp.623–628, June 1999). And since VEGF directly promotes osteoclastic bone resorption through KDR/Flk-1 expressed in mature osteoclasts (FEBS Let. 473:161–164 (2000); Endocrinology, 141:1667 (2000)), the instant compounds are also useful to treat and prevent conditions related to bone resorption, such as osteoporosis and Paget's disease.

The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265–270(1998); *J. Clin. Invest.* 104:1613–1620(1999)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, in the case of bone-related disorders, combinations that would be useful include those with antiresorptive bisphosphonates, such as alendronate and risedronate; integrin blockers (defined further below), such as $\alpha_v\beta_3$ antagonists; conjugated estrogens used in hormone replacement therapy, such as PREMPRO®, PREMARIN® and ENDOMETRION®; selective estrogen receptor modulators (SERMs), such as raloxifene, droloxifene, CP-336,156 (Pfizer) and lasofoxifene; cathespin K inhibitors; and ATP proton pump inhibitors.

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, N-4-carboxyphenyl retinamide, "Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methylpyridine) platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyldaunorubicin.

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidenechartreusin, 9-methoxy-N,N-dimethyl-5-nitropyrazolo[3,4,5-kl] acridine-2-(6H)propanamine, 1-amino-9-ethyl-5-fluoro-2,3-dihydro-9-hydroxy-4-methyl-1H, 12H-benzo[de]pyrano[3', 4':b,7]indolizino[1,2b]quinoline-10,13(9H,15H) lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl) amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

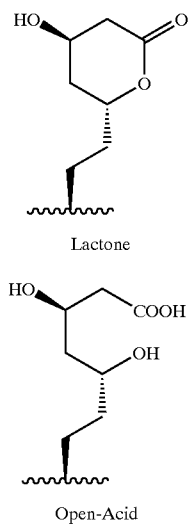

Lactone

Open-Acid

In HMG-COA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2 (1H)-quinolinone, (−)-6-[amino(4-chlorophenyl)(1-methyl-1H-imidazol-5-yl)methyl]-4-(3-chlorophenyl)-1-methyl-2 (1H)-quinolinone, (+)-6-[amino(4-chlorophenyl)(1-methyl-1H-imidazol-5-yl)methyl]-4-(3-chlorophenyl)-1-methyl-2 (1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl] piperidine, 4-{5-[4-Hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl) benzyl]-3H-imidazol-4-ylmethyl}benzonitrile, 4-{3-[4-(5-chloro-2-oxo-2H-[1,2']bipyridin-5'-ylmethyl]-3H-imidazol- 4-ylmethyl}benzonitrile, 4-{3-[4-(2-Oxo-2H-[1,2']bipyridin-5'-ylmethyl]-3H-imidazol-4-ylmethyl}benzonitrile, 4-{3-(2-Oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclononadecine-9-carbonitrile, (±)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-Dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Pat. Publ. 0 618 221, European Pat. Publ. 0 675 112, European Pat. Publ. 0 604 181, European Pat. Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp.1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalnol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF. (see, Nature Biotechnology, Vol. 17, pp.963–968 (October 1999); Kim et al., Nature, 362, 841–844 (1993)).

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RP14610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

ASSAYS

The compounds of the instant invention described in the Examples were tested by the assays described below and were found to have kinase inhibitory activity. Other assays are known in the literature and could be readily performed by those of skill in the art. (see, for example, Dhanabal et al., Cancer Res. 59:189–197; Xin et al., J. Biol. Chem. 274:9116–9121; Sheu et al., Anticancer Res. 18:4435–4441; Ausprunk et al., Dev. Biol. 38:237–248; Gimbrone et al., J. Natl. Cancer Inst. 52:413–427; Nicosia et al., In Vitro 18:538–549).

I. VEGF RECEPTOR KINASE ASSAY

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

MATERIALS

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10 % glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10 % glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50 % glycerol, 10 mg/mL of each leupeptin, pepstatin and aprotinin and 1 mM phenylmethylsuflonyl fluoride.

10×reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10×Substrate: 750 µg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

METHOD

A. Protein Purification

1. Sf21 cells were infected with recombinant virus at a multiplicity of infection of 5 virus particles/ cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 µl of inhibitor or control to the assay in 50% DMSO.

2. Add 35 μl of reaction mix containing 5 μl of 10×reaction buffer, 5 μl 25 mM ATP/10 μCi [$^{33}$P]ATP (Amersham), and 5 μl 10×substrate.
3. Start the reaction by the addition of 10 μl of KDR (25 nM) in enzyme dilution buffer.
4. Mix and incubate at room temperature for 15 minutes.
5. Stop by the addition of 50 μl stop solution.
6. Incubate for 15 minutes at 4° C.
7. Transfer a 90 μl aliquot to filter plate.
8. Aspirate and wash 3 times with wash solution.
9. Add 30 μl of scintillation cocktail, seal plate and count in a Wallac Microbeta scintillation counter.

II. HUMAN UMBILICAL VEIN ENDOTHELIAL CELL MITOGENESIS ASSAY

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

MATERIALS

HUVECs: HUVECs frozen as primary culture isolates are obtained from Clonetics Corp. Cells are maintained in Endothelial Growth Medium (EGM; Clonetics) and are used for mitogenic assays described in passages 3–7 below.
Culture Plates: NUNCLON 96-well polystyrene tissue culture plates (NUNC #167008).
Assay Medium: Dulbecco's modification of Eagle's medium containing 1 g/mL glucose (low-glucose DMEM; Mediatech) plus 10% (v/v) fetal bovine serum (Clonetics).
Test Compounds: Working stocks of test compounds are diluted serially in 100% dimethylsulfoxide (DMSO) to 400-fold greater than their desired final concentrations. Final dilutions to 1×concentration are made directly into Assay Medium immediately prior to addition to cells.
10×Growth Factors: Solutions of human VEGF$_{165}$ (500 ng/mL; R&D Systems) and bFGF (10 ng/mL; R&D Systems) are prepared in Assay Medium.
10×[$^3$H]Thymidine: [Methyl-$^3$H]thymidine (20 Ci/mmol; Dupont-NEN) is diluted to 80 μCi/mL in low-glucose DMEM.
Cell Wash Medium: Hank's balanced salt solution (Mediatech) containing 1 mg/mL bovine serum albumin (Boehringer-Mannheim).
Cell Lysis Solution: 1 N NaOH, 2% (w/v) Na$_2$CO$_3$.

METHOD

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% CO$_2$.
2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% CO$_2$ for 2 hours to allow test compounds to enter cells.
3. After the 2-hour pretreatment period, cells are stimulated by addition of 10 μL/well of either Assay Medium, 10×VEGF solution or 10×bFGF solution. Cells are then incubated at 37° C. and 5% CO$_2$.
4. After 24 hours in the presence of growth factors, 10×[$^3$H]thymidine (10 μL/well) is added.
5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of Formula I are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 0.01–5.0 μM. These compounds also show selectivity over related tyrosine kinases (e.g., FGFR1 and the Src family; for relationship between Src kinases and VEGFR kinases, see Eliceiri et al., Molecular Cell, Vol. 4, pp.915–924, December 1999).

EXAMPLES

Examples provided are intended to assist in a further understanding of the invention. Particular materials employed, species and conditions are intended to be illustrative of the invention and not limiting of the reasonable scope thereof.

SCHEME 1

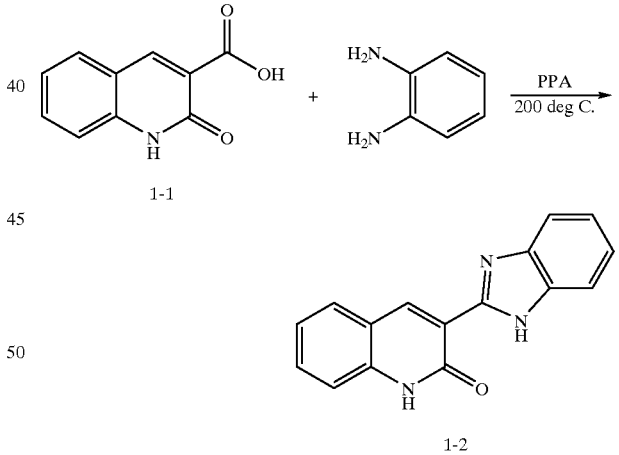

3-(Benzoimidazol-2-yl)-quinolin-2-one (1-2)

A suspension of 2-oxo-1,2-dihydroquinoline-3-carboxylic acid 1-1 (500 mg, 2.64 mmol, 1 equiv, prepared by the method of Marsais, F; Godard, A.; Queguiner, G. *J. Heterocyclic Chem.* 1989, 26,1589) and 1,2-phenylenediamine (344 mg, 3.18 mmol, 1.20 equiv) in polyphosphoric acid (15 mL) was heated under argon at 200° C. for 4.5 h. The hot reaction mixture was poured over ice (200 g), and the resulting mixture was allowed to stand overnight (20 h). The precipitate was filtered, washed with water (200 mL), and air dried to give the title compound as an olive-colored solid. $^1$H NMR (400 MHz, (CD$_3$)$_2$SO) δ

12.58 (s, 1H), 9.15 (s, 1H), 7.94 (br d, 1H, J=7.5 Hz), 7.78 (dd, 2H, J=5.6, 2.9), 7.63 (br t, 1H, J=7.5 Hz), 7.42 (br d, 1H, J=8.2 Hz), 7.33 (dd, 2H, J=5.9, 2.9), 7.25 (br t, 1H, J=7.5 Hz); HRMS (electrospray FT/ICR) calculated for $C_{16}H_{12}N_3O$ [M+H]$^+$ 262.0975, found 262.0981; anal. calcd for $C_{16}H_{11}N_3O+1.10$ $H_3PO4+0.75$ $H_2O$: C, 50.23; H, 4.16; N, 10.98. Found C, 50.24; H, 4.21; N, 10.93.

Compounds 1-3 through 1-6 below were synthesized via the same protocol shown in Scheme 1 by using the appropriately substituted phenylenediamine.

3-(5-Methyl-benzoimidazol-2-yl)-quinolin-2-one (1-3)

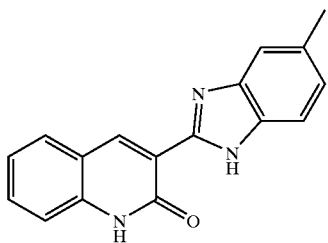

A suspension of 2-oxo-1,2-dihydro-quinoline-3-carboxylic acid 1-1 (500 mg, 2.64 mmol, 1 equiv) and 3,4-diaminotoluene (646 mg, 5.29 mmol, 2.00 equiv) in polyphosphoric acid (10 mL) was heated under argon at 200° C. for 2 h. The hot reaction mixture was poured over ice (200 g), and the resulting mixture was allowed to stand until all polyphosphoric acid had dissolved. The precipitate was filtered, washed with water (200 mL), and air dried. The olive-colored solid was partitioned between aqueous sodium bicarbonate solution (200 mL) and ethyl acetate (200 mL). The organic layer was dried over sodium sulfate and concentrated to give 1-3 as a yellow solid. $^1$H NMR (300 MHz, CDCl$_3$) major hydrogen-bonded rotational isomer: δ 15.20 (br s, 1H), 14.30 (br s, 1H), 9.18 (s, 1H), 7.77 (br d, 1H, J=7.6 Hz), 7.61 (br d, 1H, J=7.5 Hz), 7.60 (br t, 1H, J=7.5 Hz), 7.37 (br s, 1H), 7.36 (br d, 1H, J=7.5 Hz), 7.32 (br t, 1H, J=7.6), 7.14 (br d, 1H, J=8.2 Hz), 2.52 (s, 3H); HRMS (electrospray FT/ICR) calcd for $C_{17}H_{14}N_3O$ [M+H]$^+$ 276.1131, found 276.1132; TLC (40% EtOAc in hexane) R$_f$=0.10.

3-(5,6-Dimethyl-benzoimidazol-2-yl)-quinolin-2-one (1-4)

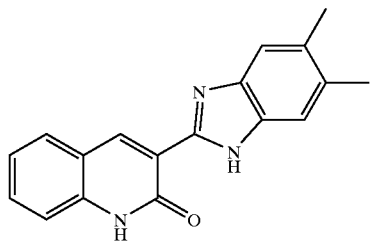

A suspension of 2-oxo-1,2-dihydro-quinoline-3-carboxylic acid 1-1 (300 mg, 1.59 mmol, 1 equiv) and 4,5-dimethyl-1,2-phenylenediamine (432 mg, 3.17 mmol, 2.00 equiv) in polyphosphoric acid (10 mL) was heated under argon at 200° C. for 1.5 h. The hot reaction mixture was poured over ice (100 g), and the resulting mixture was allowed to stand until all polyphosphoric acid had dissolved. The precipitate was filtered, washed with water (100 mL), and air dried. The olive-colored solid was partitioned between aqueous sodium bicarbonate solution (500 mL) and ethyl acetate (500 mL) aided by sonication. The organic layer was dried over sodium sulfate and concentrated to give 1-4 as a yellow solid. $^1$H NMR (300 MHz, (CD$_3$)$_2$SO) δ 12.63 (br s, 1H), 12.46 (br s, 1H), 9.01 (s, 1H), 7.91 (br d, 1H, J=7.3 Hz), 7.57 (td, 1H, J=8.2, 1.2 Hz), 7.43 (br s, 2H), 7.41 (br d, 1H, J=7.6 Hz), 7.25 (br t, 1H, J=7.3), 2.32 (s, 6H); HRMS (electrospray FT/ICR) calculated for $C_{18}$—$H_{16}N_3O$ [M+H]$^+$ 290.1288, found 290.1286.

3-(5-Fluoro-benzoimidazol-2-yl)-quinolin-2-one (1-5)

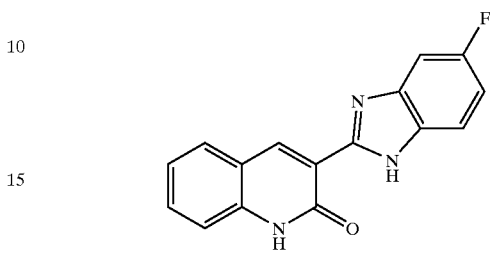

A suspension of 2-oxo-1,2-dihydro-quinoline-3-carboxylic acid 1-1 (300 mg, 1.59 mmol, 1 equiv) and 4-fluoro-1,2-phenylenediamine (400 mg, 3.17 mmol, 2.00 equiv) in polyphosphoric acid (10 mL) was heated under argon at 200° C. for 1.5 h. The hot reaction mixture was poured over ice (100 g), and the resulting mixture was allowed to stand until all polyphosphoric acid had dissolved. The precipitate was filtered, washed with water (100 mL), and air dried. The redish solid was partitioned between aqueous sodium bicarbonate solution (200 mL) and ethyl acetate (200 mL) aided by sonication. The organic layer was dried over sodium sulfate and concentrated to give 1-5 as a red solid. $^1$H NMR (400 MHz, (CD$_3$)$_2$SO) major hydrogen-bonded rotational isomer δ 12.75 (br s, 1H), 12.48 (br s, 1H), 9.11 (s, 1H), 7.96 (br d, 1H, J=7.9 Hz), 7.69 (br dd, 1H, J=8.5, 5.1), 7.63 (br t, 1H, J=7.5 Hz), 7.49 (br d, 1H, J=8.8 Hz), 7.45 (br d, 1H, J=8.1 Hz), 7.30 (br t, 1H, J=7.5 Hz), 7.08 (br d, 1H, J=9.2 Hz); HRMS (electrospray FT/ICR) calculated for $C_{16}$—$H_{11}FN3O$ [M+H]$^+$ 280.0881, found 280.0890.

3-(4-Methyl-benzoimidazol-2-yl)-quinolin-2-one (1-6)

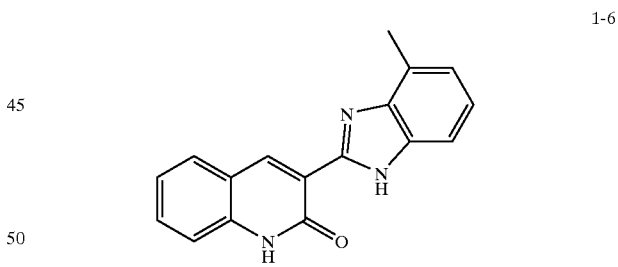

Oxalyl chloride (3.7 mL, 42 mmol, 8.0 equiv) and DMF (20 μL, cat.) were added sequentially to a suspension of 2-oxo-1,2-dihydro-quinoline-3-carboxylic acid (1.0 g, 5.30 mmol, 1 equiv) in CH$_2$Cl$_2$ (35 mL) at 23° C., and the resulting mixture was stirred for 1 h. Gas evolution was observed while the reaction mixture became homogeneous over this period of time. The resulting solution was concentrated to give a white solid (1.34 g). To a solution of a fraction of this solid (50 mg, 0.19 mmol) in dichloromethane (5 mL) was sequentially added 2,3-diaminotoluene (41 mg, 0.33 mmol) and N,N-diisopropylethylamine (135 μL, 0.774 mmol). The resulting mixture was stirred at 23° C. for 1 h, then partitioned between aqueous saturated sodium bicarbonate solution (100 mL) and dichloromethane (2×50 mL). The combined organic layers were dried over sodium sulfate and concentrated. A mixture of the residue and polyphosphoric acid (5 mL) was heated at 200° C. for 2 h. The hot mixture was then poured over ice (50 g) and allowed to stand for 20 h. The aqueous mixture was basified to pH 5 with solid sodium bicarbonate, then extracted with ethyl acetate (3×50 mL). The combined organic layers were dried over sodium sulfate and concentrated, and the residue was purified by reverse-phase HPLC ($H_2O/CH_3CN$ w/0.1% TFA) to give 1-6 as a trifluoroacetic acid salt. The salt was partitioned between aqueous sodium bicarbonate solution (50 mL) and ethyl actetate (50 mL), and the organic layer was dried over sodium sulfate and concentrated to give free 1-6 as an off-white solid. $^1$H NMR (300 MHz, $(CD_3)_2SO$) δ 9.07 (s, 1H), 8.05 (br d, 1H, J=7.7 Hz), 7.62 (br t, 1H, J=7.1 Hz), 7.54 (br d, 1H, J=7.7 Hz), 7.44 (br d, 1H, J=7.7 Hz), 7.30 (br t, 1H, J=7.3 Hz), 7.09 (t, 1H, J=7.7 Hz), 7.01 (br d, 1H, J=7.3 Hz), 2.61 (s, 3H); HRMS (electrospray FT/ICR) calculated for $C_{17}H_{14}N_3O$ [M+H]$^+$ 276.1131, found 276.1142.

the resulting blue mixture was stirred for 10 min. 1-(2-chloroethyl)piperidine monohydrochloride (2.50 g, 13.6 mmol, 1.10 equiv) was added, and the resulting mixture was heated at 50 ° C. for 20 h. The reaction mixture was cooled to 23° C., then partitioned between water (800 mL) and ethyl acetate (3×200 mL). The combined organic layers were washed with aqueous saturated sodium carbonate solution (500 mL) then brine (500 mL), then dried over sodium sulfate and concentrated. The residue was purified by flash column chromatography (5% MeOH in $CH_2Cl_2$) to give 2-2 as a dark orange oil. $^1$H NMR (300 MHz, $CDCl_3$) δ 7.58 (d, 1H, J=2.2 Hz), 7.10 (dd, 1H, J=9, 2.2 Hz), 6.75 (d, 1H, J=9.2 Hz), 5.90 (br s, 2H), 4.06 (t, 2H, J=6.0 Hz), 2.79 (t, 2H, J=6.0 Hz), 2.52 (m, 4H), 1.62 (m, 4H), 1.44 (m, 2H). TLC (5% MeOH in $CH_2Cl_2$), $R_f$=0.14.

Synthesis of 2-3:

A mixture of 2-2 (2.9 g, 10.9 mmol, 1 equiv) and zinc powder (7.1 g, 109 mmol, 10 equiv) in glacial acetic acid

SCHEME 2

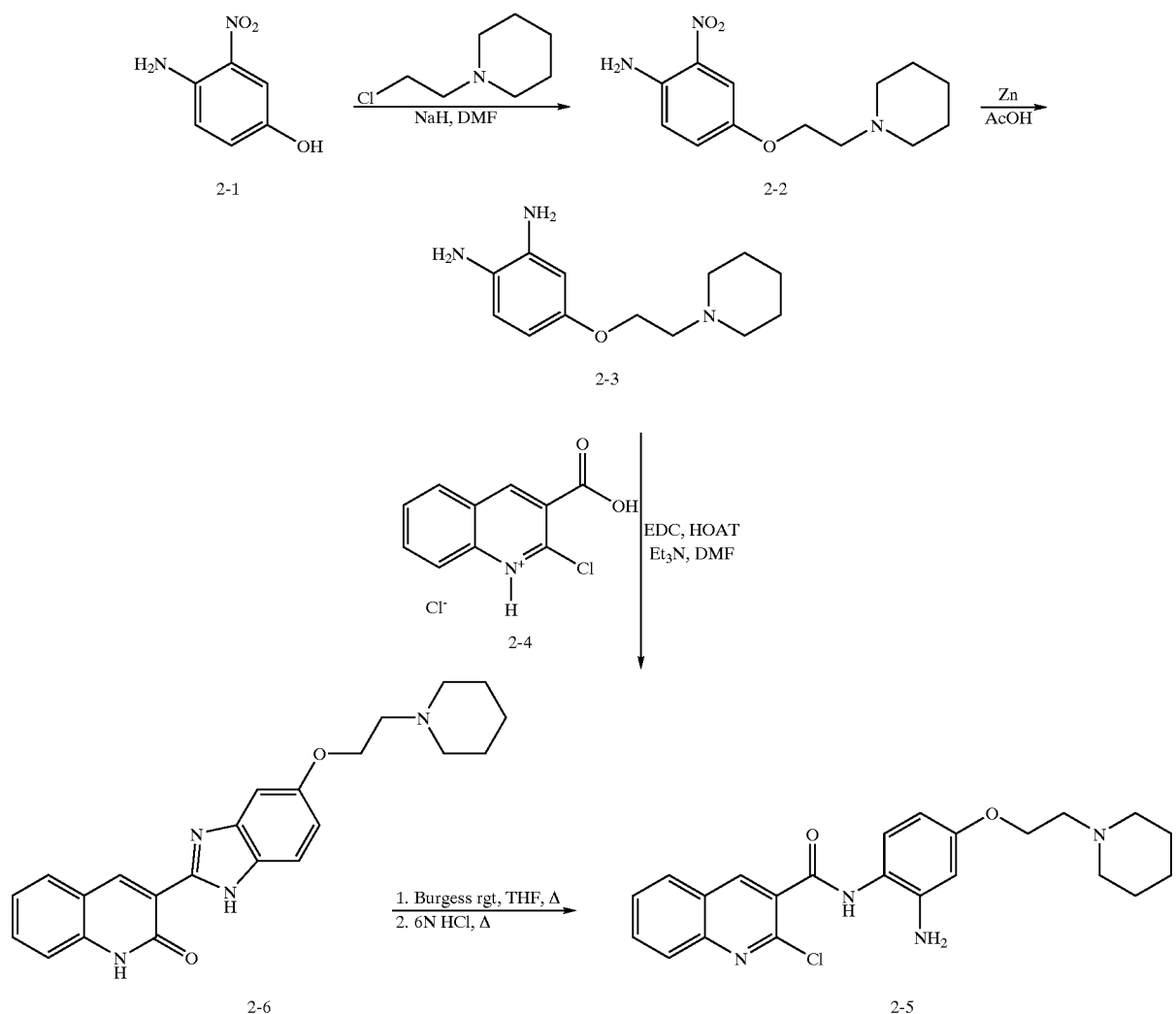

Synthesis of 2-2:

Sodium hydride (95%, 700 mg, 27.7 mmol, 2.25 equiv) was added carefully to a solution of 4-amino3-nitrophenol (1.90 g, 12.3 mmol, 1 equiv) in DMF (30 mL) at 23° C. and (100 mL) was heated at 60° C. for 1 h. Additional zinc powder was added (7.1 g, 109 mmol, 10 equiv) and heating at 60 ° C. was continued for 1 h. The solids were filtered onto a pad of Celite® and washed with acetic acid (100 mL). The combined filtrate was concentrated, and the residue was repeatedly (2×) redissolved in toluene (100 mL) and concentrated to give 2-3 as a multiacetic acid salt (6.2 g, viscous oil). Half of this product (3.1 g) was partitioned between aqueous 1N NaOH solution (200 mL) and dichloromethane (200 mL). The organic layer was dried over sodium sulfate and concentrated to give 2-3 as its free base. $^1$H NMR (300 MHz, CD$_3$OD) multiacetic acid salt δ 6.75 (d, 1H, J=8.5 Hz), 6.47 (d, 1H, J=2.4 Hz), 6.33 (dd, 1H, J=8.5, 2.4 Hz), 4.23 (t, 2H, J=4.7 Hz), 3.42 (t, 2H, J=4.7 Hz), 3.44 (m, 4H), 1.86 (m, 4H), 1.67 (m, 2H).

Synthesis of 2-5:

A mixture of 2-chloro-quinoline-3-carboxylic acid hydrochloride (2-4, 1.0 g, 4.1 mmol, 1 equiv, prepared by the method of Marsais, F; Godard, A.; Queguiner, G. *J. Heterocyclic Chem*. 1989, 26, 1589), 2-3 (1.2 g, 5.1 mmol, 1.2 equiv), 1-(3-dimethylaminopropyl)-3-ethylcarbodiimide hydrochloride (920 mg, 4.8 mmol, 1.2 equiv), 1-hydroxy-7-azabenzotriazole (650 mg, 4.8 mmol, 1.2 equiv), and triethylamine (1.3 mL, 9.6 mmol, 2.3 equiv) in DMF (50 mL) was stirred at 23° C. for 72 h. The reaction mixture was concentrated, and the residue was partitioned between ethyl actate (200 mL) and aqueous saturated sodium bicarbonate solution (200 mL). The organic layer was washed with aqueous saturated sodium bicarbonate solution (2×200 mL), then dried over sodium sulfate and concentrated. The residue was purified by flash column chromatography (CH$_2$Cl$_2$ initially, grading to 10% MeOH in CH$_2$Cl$_2$) to give 2-5 as a light yellow solid. $^1$H NMR (300 MHz, CDCl$_3$) δ 8.66 (s, 1H), 8.06 (br d, 1H, J=7.8 Hz), 8.04 (br s, 1H), 7.91 (br d, 1H, J=7.8 Hz), 7.84 (td, 1H, J=6.8, 1.8 Hz), 7.64 (td, 1H, J=6.8, 1.8 Hz), 7.23 (d, 1H, J=7.8 Hz), 6.41 (dd, 1H, J=7.8, 2.7 Hz), 6.39 (s, 1H), 4.09 (t, 2H, J=5.4 Hz), 3.98 (br s, 2H), 2.77 (t, 2H, J=5.4 Hz), 2.53 (m, 4H), 1.63 (m, 4H), 1.46 (m, 2H).

Synthesis of 3-[5-(2-Piperidin-1-yl-ethoxy)-benzimidazol-2-yl]-quinolin-2-one (2-6):

A solution of 2-5 (150 mg, 0.353 mmol, 1 equiv) and (methoxycarbonylsulfamoyl)triethylammonium hydroxide, inner salt, (Burgess reagent, 252 mg, 1.06 mmol, 3.00 equiv) in THF (15 mL) was heated at reflux for 30 minutes. Additional Burgess reagent (84 mg, 0.35 mmol, 1.0 equiv) was added and heating was continued for 30 minutes. The reaction mixture was cooled to 23° C., then partitioned between water (150 mL) and CH$_2$Cl$_2$ (2×100 mL). The combined organic layers were dried over sodium sulfate and concentrated. The residue was dissolved in a 1:1 mixture (20 mL) of dioxane and aqueous 6 N hydrochloric acid solution, and the resulting solution was heated at 90° C. for 16 h. The reaction mixture was cooled to 23° C., then partitioned between aqueous 1N sodium hydroxide solution (100 mL) and CH$_2$Cl$_2$ (2×100 mL). The combined organic layers were dried over sodium sulfate and concentrated. The residue was purified by flash column chromatography (5% MeOH in CH$_2$Cl$_2$ initially, grading to 15% MeOH in CH$_2$Cl$_2$) to give the title as a yellow solid. $^1$H NMR (400 MHz, CD$_3$OD) δ 8.88 (s, 1H), 7.82 (d, 1H, J=7.9 Hz), 7.60 (t, 1H, J=7.3 Hz), 7.54 (d, 1H, J=8.8 Hz), 7.40 (d, 1H, J=8.2 Hz), 7.32 (t, 1H, J=7.7 Hz), 7.17 (br s, 1H), 6.94 (dd, 1H, J=8.8, 1.8 Hz), 4.20 (t, 2H, J=5.5 Hz), 2.88 (t, 2H, J=5.5 Hz), 2.65 (m, 4H), 1.67 (m, 4H), 1.52 (m, 2H). HRMS (electrospray FT/ICR) calculated for C$_{23}$H$_{25}$N$_4$O$_2$ [M+H]$^+$ 389.1972, found 389.1952.

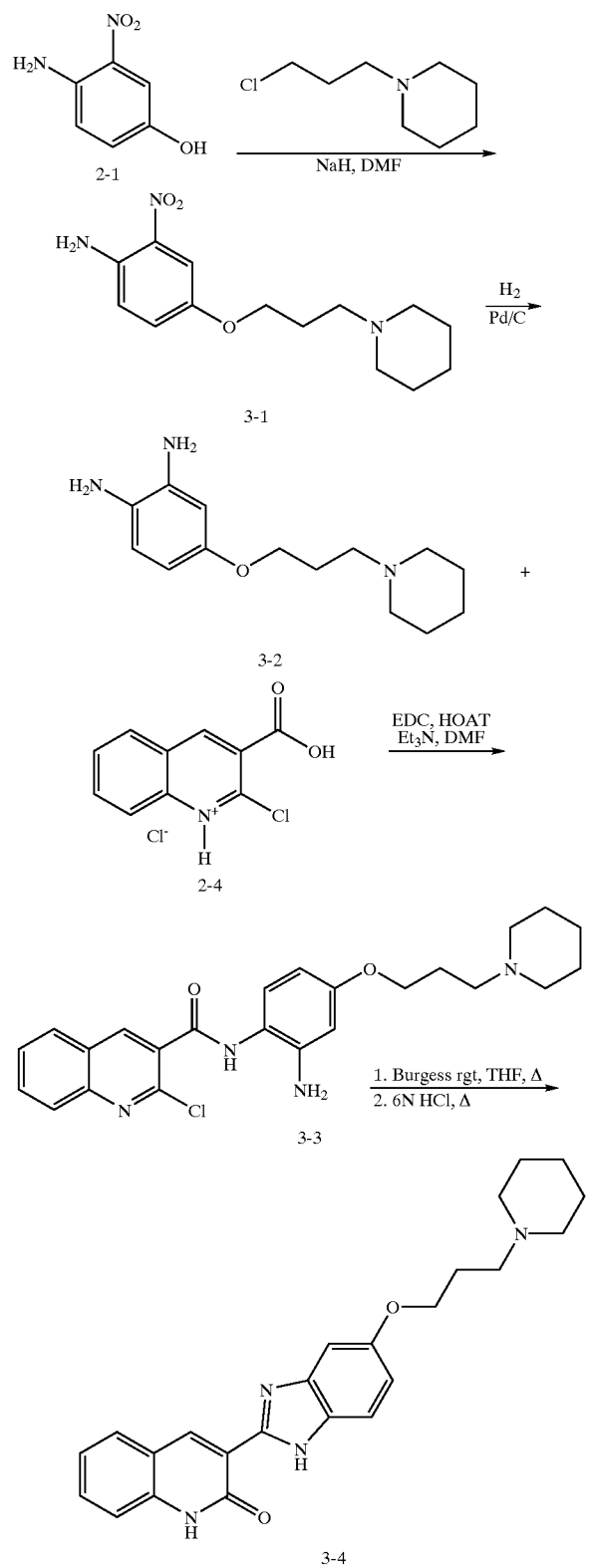

SCHEME 3

Synthesis of 3-1:

Sodium hydride (95%, 660 mg, 26.1 mmol, 2.04 equiv) was added carefully to a solution of 4-amino3-nitrophenol (2.00 g, 12.8 mmol, 1 equiv) in DMF (50 mL) at 23° C. and the resulting blue mixture was stirred for 10 min. 1-(2-chloropropyl)piperidine monohydrochloride (2.66 g, 13.4 mmol, 1.05 equiv) was added, and the resulting mixture was heated at 50° C. for 4 h. The reaction mixture was cooled to 23° C., then partitioned between aqueous 1N sodium hydroxide solution (500 mL) and dichloromethane (4×200 mL). The combined organic layers were dried over sodium sulfate and concentrated to give 3-1 as a yellow oil which crystallized upon standing. $^1$H NMR (400 MHz, CDCl$_3$) δ 7.55 (d, 1H, J=2.8 Hz), 7.07 (dd, 1H, J=9.0, 2.9 Hz), 6.75 (d, 1H, J=9.1 Hz), 5.86 (br s, 2H), 3.98 (t, 2H, J=6.4 Hz), 2.46 (t, 2H, J=7.3 Hz), 2.40 (m, 4H), 1.96 (p, 2H, J=7.0 Hz), 1.59 (m, 4H), 1.44 (m, 2H).

Synthesis of 3-2:

A mixture of 3-1 (2.80 g, 10.0 mmol, 1 equiv) and 10% Pd/C (2.00 g, 1.88 mmol in Pd, 0.188 equiv) in ethyl acetate (100 mL) was stirred under a hydrogen balloon for 16 h. The catalyst was filtered onto a pad celite and washed with ethyl acetate (300 mL). The combined filtrate was concentrated to give 3-2 as a colorless oil. 1H NMR (300 MHz, CDCl$_3$) δ 6.65 (d, 1H, J=8.3 Hz), 6.33 (d, 1H, J=2.4 Hz), 6.26 (dd, 1H, J=8.3, 2.7 Hz), 3.91 (t, 2H, J=6.4 Hz), 3.50 (br s, 2H), 3.06 (br s, 2H), 2.45 (t, 2H, J=7.3 Hz), 2.39 (m, 4H), 1.93 (p, 2H, J=7.1 Hz), 1.59 (m, 4H), 1.44 (m, 2H).

Synthesis of 3-3:

A mixture of 2-chloro-quinoline-3-carboxylic acid hydrochloride (2-4, 1.5 g, 6.1 mmol, 1 equiv, prepared by the method of Marsais, F; Godard, A.; Queguiner, G. J. Heterocyclic Chem. 1989, 26, 1589), 3-2 (2.3 g, 9.2 mmol, 1.5 equiv), 1-(3-dimethylaminopropyl)-3-ethylcarbodiimide hydrochloride (1.4 g, 7.3 mmol, 1.2 equiv), 1-hydroxy-7-azabenzotriazole (1.0 g, 7.3 mmol, 1.2 equiv), and triethylamine (2.6 mL, 18 mmol, 3.0 equiv) in DMF (100 mL) was stirred at 23° C. for 6 h. The reaction mixture was concentrated, and the residue was partitioned between water (500 mL) and ethyl acetate (2×300 mL). The organic layer was washed with aqueous saturated sodium bicarbonate solution (2×200 mL) and brine (200 mL), then dried over sodium sulfate and concentrated. The residue was suspended in hexanes (200 mL) with the aid of sonication, and the solids filtered to give 3-3 as a dirty brown solid. 1H NMR (400 MHz, CDCl$_3$) δ 8.69 (s, 1H), 8.07 (br d, 1H, J=7.8 Hz), 7.97 (br s, 1H), 7.92 (br d, 1H, J=7.8 Hz), 7.84 (td, 1H, J=6.8, 1.8 Hz), 7.64 (td, 1H, J=6.8, 1.8 Hz), 7.23 (d, 1H, J=7.8 Hz), 6.41 (dd, 1H, J=7.8, 2.7 Hz), 6.39 (s, 1H, 3.98 (t, 2H, J=6.0 Hz), 3.98 (br s, 2H), 2.47 (t, 2H, J=7.2 Hz), 2.40 (m, 4H), 1.97 (p, 1H, J=7.2 Hz), 1.60 (m, 4H), 1.46 (m, 2H).

Synthesis of 3-[5-(2-Piperidin-1-yl-propoxy)-benzimidazol-2-yl]-quinolin-2-one (3-4):

(Methoxycarbonylsulfamoyl)triethylammonium hydroxide, inner salt, (Burgess rgt, 814 mg, 3.42 mmol, 3.00 equiv) was added to a solution of 3-3 (500 mg, 1.14 mmol, 1 equiv) in THF (20 mL) at reflux, and the resulting mixture was heated at reflux for 10 min. Additional Burgess reagent (814 mg, 3.42 mmol, 3.00 equiv) was added and heating was continued for 30 minutes. The reaction mixture was cooled to 23° C., then partitioned between half-saturated aqueous sodium bicarbonate solution (100 mL) and ethyl acetate (2×100 mL). The aqueous layer was further extracted with dichloromethane (2×100 mL), then the combined organic layers were dried over sodium sulfate and concentrated. The residue was dissolved in a 1:1 mixture (20 mL) of dioxane and aqueous 6 N hydrochloric acid solution, and the resulting solution was heated at reflux for 1 h. The reaction mixture was cooled to 23° C., then partitioned between aqueous 1N sodium hydroxide solution (150 mL) and CH$_2$Cl$_2$ (2×100 mL). The combined organic layers were dried over sodium sulfate and concentrated. The residue was purified by flash column chromatography (10% MeOH in CH$_2$Cl$_2$) to give 3-4 as a yellow solid. $^1$H NMR (400 MHz, CD$_3$OD) δ 8.91 (s, 1H), 7.84 (d, 1H, J=7.9 Hz), 7.62 (td, 1H, J=7.3, 1.2 Hz), 7.54 (d, 1H, J=8.8 Hz), 7.41 (d, 1H, J=8.2 Hz), 7.33 (t, 1H, J=7.7 Hz), 7.17 (d, 1H, J=2.1 Hz), 6.92 (dd, 1H, J=8.8, 2.4 Hz), 4.08 (t, 2H, J=6.2 Hz), 2.58 (t, 2H, J=7.8 Hz), 2.50 (m, 4H), 2.05 (m, 2H), 1.64 (m, 4H), 1.50 (m, 2H). HRMS (electrospray FT/ICR) calculated for C$_{24}$H27N$_4$O$_2$ [M+H]$^+$ 403.2128, found 403.2128.

SCHEME 4

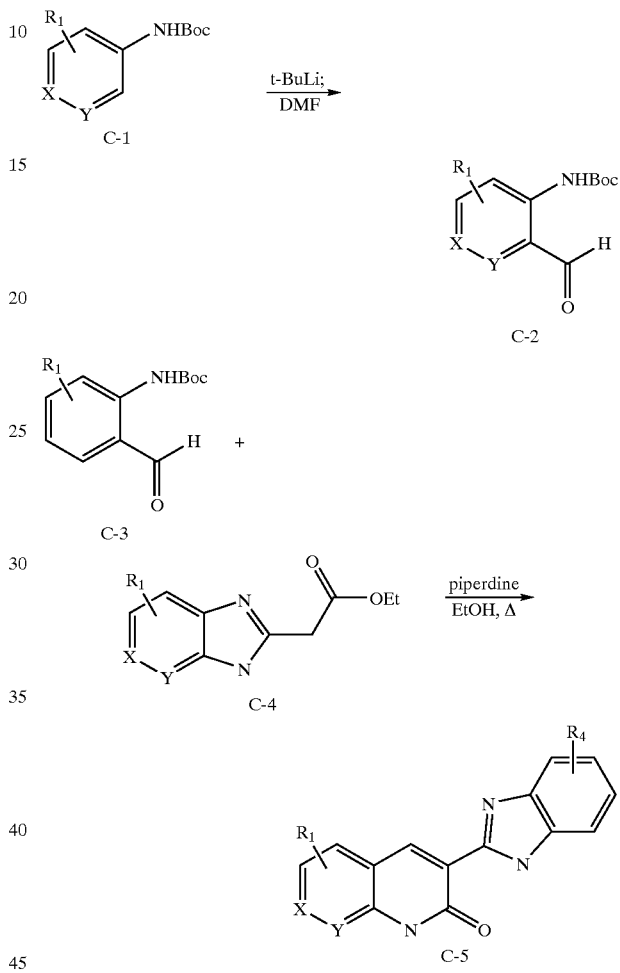

Synthesis of 4-3:

Oxalyl chloride (3.0 mL, 34 mmol, 8.3 equiv) and DMF (10 μL, cat.) were added sequentially to a suspension of 2-chloro-quinoline-3-carboxylic acid hydrochloride (1.0 g, 4.1 mmol, 1 equiv) in CH$_2$Cl$_2$ (50 mL) at 23° C., and the resulting mixture was stirred for 1 h. Gas evolution was observed while the reaction mixture became homogeneous over this period of time. The resulting solution was concentrated. A solution of the residue in CH$_2$Cl$_2$ (30 mL) was then added to a solution of methyl 3,4-diaminobenzoate (800 mg, 4.8 mmol, 1.2 equiv) and N,N-diisopropylethylamine (1.2 mL, 6.9 mmol, 1.7 equiv) in CH$_2$Cl$_2$ (30 mL) at 23° C. The resulting solution was stirred for 30 min, during which time a fine white precipitate formed. The reaction mixture was partitioned between aqueous saturated sodium bicarbonate solution (100 mL) and CH$_2$Cl$_2$ (100 mL). The suspended precipitate within the organic layer was filtered onto a glass frit, washed with CH$_2$Cl$_2$ (100 mL), and allowed to air dry to give 4-3 as a white solid. $^1$H NMR (300 MHz, CD$_3$OD) δ 8.73 (s, 1H), 8.10 (br d, 1H, J=7.9 Hz), 8.03 (br d, 1H, J=7.9 Hz), 8.02 (d, 1H, J=1.9 Hz), 7.92 (td, J=7.3, 1.6 Hz), 7.77 (dd, 1H, J=8.5, 1.9 Hz), 7.74 (br t, 1H, J=7.1 Hz), 6.89 (d, 1H, J=8.5 Hz), 3.87 (s, 3H).

Synthesis of 4-4:

A solution of 4-3 (400 mg, 1.12 mmol, 1 equiv) and (methoxycarbonylsulfamoyl)triethylammonium hydroxide, inner salt, (Burgess reagent, 800 mg, 3.37 mmol, 3.00 equiv) in THF (30 mL) at reflux for 1 h. Additional Burgess reagent (800 mg, 3.37 mmol, 3.00 equiv) was then added in two equal portions (400 mg) while heating was continued for 1 h. The reaction mixture was allowed to cool, then partitioned between water (300 mL) and ethyl acetate (300 mL). The organic layer was dried over sodium sulfate and concentrated. The residue was purified by flash column chromatography (100% EtOAc) to give 4-4 as a white solid. $^1$H NMR (300 MHz, CD$_3$OD) δ 8.83 (s, 1H), 8.39 (br s, 1H), 8.09 (br d, 1H, J=9.1 Hz), 8.04 (br d, 1H, J=8.8 Hz), 8.02 (dd, J=9.2, 1.7 Hz), 7.92 (td, 1H, J=7.8, 1.8 Hz), 7.74 (d, 1H, J=8.2 Hz), 7.73 (td, 1H, J=7.8, 1.8 Hz), 3.97 (s, 3H).

2-(2-oxo-1,2-Dihydro-quinolin-3-yl)-benzoimidazole-5-carboxylic Acid Methyl Ester (4-5) and 2-(2-oxo-1,2-Dihydro-quinolin-3-yl)-benzoimidazole-5-carboxylic Acid (4-6):

A solution of 4-4 (20 mg, 0.059 mmol, 1 equiv) in a 1:1 mixture (30 mL) of aqueous 6 N hydrochloric acid solution and dioxane was heated at reflux for 4 h. The reaction mixture was cooled to 23° C. and basified to pH 12 with aqueous 1 N sodium hydroxide solution. The resulting aqueous mixture was extracted with dichloromethane (3×100 mL). The combined organic layers were dried over sodium sulfate and concentrated. The residue was purified by flash column chromatography (100% ethyl acetate) to give 4-5 as a white solid. The aqueous layer was acidified to pH 2 with aqueous 1 N hydrochloric acid and extracted with dichloromethane (3×100 mL). The combined organic layers were dried over sodium sulfate and concentrated. The residue was suspended in chloroform (10 mL) aided by sonification, then filtered and air dried to give 4-6 as a white solid. 4-5 Spectra: $^1$H NMR (300 MHz, CDCl$_3$) δ 9.73 (br s, 1H), 9.25 (s, 1H), 8.43 (br s, 1H), 8.04 (br d, 1H, J=8.3 Hz), 7.83 (br d, 1H, J=8.1 Hz), 7.65 (br t, 1H, J=7.5 Hz), 7.40–7.26 (m, 3H), 3.97 (s, 3H); HRMS (electrospray FT/ICR) calcd for C18-H14N3O3 [M+H]$^+$ 320.1030, found 320.1029; TLC (100% EtOAc), R$_f$=0.49. 4-6 Spectra: $^1$H NMR (300 MHz, CD$_3$OD) δ 9.05 (s, 1H), 8.38 (d, 1H, J=1.7 Hz), 7.97 (dd, 1H, J=8.6, 1.7 Hz), 7.89 (br d, 1H, J=6.8 Hz), 7.73 (d, 1H, J=8.5 H 7.66 (br t, 1H, J=7.1 Hz), 7.45 (br d, 1H, J=8.3 Hz), 7.35 (br t, 1H, J=7.4 Hz), 3.97; HRMS (electrospray FT/ICR) calculated for C$_{17}$H$_2$N$_3$O$_3$ [M+H]$^+$ 306.0873, found 306.0870; TLC (100% EtOAc), R$_f$=0.25.

Synthesis of 4-7:

A mixture of 4-4 (210 mg, 0.622 mmol, 1 equiv) and aqueous 1 N sodium hydroxide solution (3.11 mL, 3.11 mmol, 5.00 equiv) in t-BuOH (10 mL) was heated at 55° C. for 20 h. The reaction mixture was cooled, then diluted with water (200 mL) and brine (100 mL). The resulting mixture was extracted with ethyl ether (2×200 mL, discarded), then acidified with concentrated hydrochloric acid to pH 2. The acidic solution was extracted with a 1:1 mixture of ethyl acetate and ethyl ether (3×150 mL). The combined organic layers were washed with brine (200 mL), dried over sodium sulfate, and concentrated to give 4-7 as a tan solid. 1H NMR (300 MHz, CD$_3$OD) δ 8.85 (s, 1H), 8.42 (d, 1H, J=1.4 Hz), 8.12 (br d, 1H, J=8.3 Hz), 8.06 (br d, 1H, J=8.1 Hz), 8.06 (dd, J=8.3, 1.4 Hz), 7.94 (td, 1H, J=6.8, 1.4 Hz), 7.75 (d, 1H, J=8.3 Hz), 7.74 (td, 1H, J=7.4, 1.4 Hz).

2-(2-oxo-1,2-Dihydro-quinolin-3-yl)-benzoimidazole-5-carboxylic Acid (2-Pyrrolidin-1-yl-ethyl)-amide (4-8):

A mixture of 4-7 (120 mg, 0.371 mmol, 1 equiv), 1-(2-aminoethyl) pyrrolidine (94.0 μL, 0.741 mmol, 2.00 equiv), 1-(3-dimethylaminopropyl)-3-ethylcarbodiimide hydrochloride (142 mg, 0.741 mmol, 2.00 equiv), 1-hydroxy-7-azabenzotriazole (101 mg, 0.741 mmol, 2.00 equiv), and triethylamine (103 μL, 0.741 mmol, 2.00 equiv) in DMF (5 mL) was stirred at 23 ° C. for 72 h. The reaction mixture was concentrated, and the residue was partitioned between a 1:1 mixture (100 mL) of aqueous sodium bicarbonate solution and brine and ethyl acetate (3×100 mL). The combined organic layer was dried over sodium sulfate and concentrated. The residue was suspended in ethyl ether (50 mL) aided by sonication, then filtered and air dried to give a tan solid. A suspension of the solid in a 1:1 mixture (50 mL) of aqueous 6 N hydrochloric acid solution and dioxane was heated at reflux for 5 h. The reaction mixture was diluted with water (100 mL), and the resulting aqueous mixture was basified to pH 12 with solid sodium hydroxide, then extracted with ethyl acetate (3×100 mL). The combined organic layers were dried over sodium sulfate and concentrated. The residue was suspended in ethyl ether (50 mL) aided by sonication, then filtered and air dried to give 4-8 as an off-white solid. $^1$H NMR (400 MHz, (CD$_3$)$_2$SO) δ 9.13 (s, 1H), 8.38 (br s, 1H), 8.19 (br d, 1H, J=6.8 Hz), 7.98 (br d, 1H, J=7.8 Hz), 7.73 (br s, 1H), 7.64 (td, 1H, J=7.8, 1.4 Hz), 7.45 (d, 1H, J=8.3 Hz), 7.31 (br t, 1H, J=7.3 Hz), 3.69 (m, 2H), 3.48 (m, 2H), 3.40 (m, 2H), 2.60 (m, 2H), 1.70 (m, 4H); HRMS (electrospray FT/ICR) calculated for C$_{23}$H$_{24}$N$_5$O$_2$ [M+H]$^+$ 402.1924, found 402.1928.

SCHEME 5

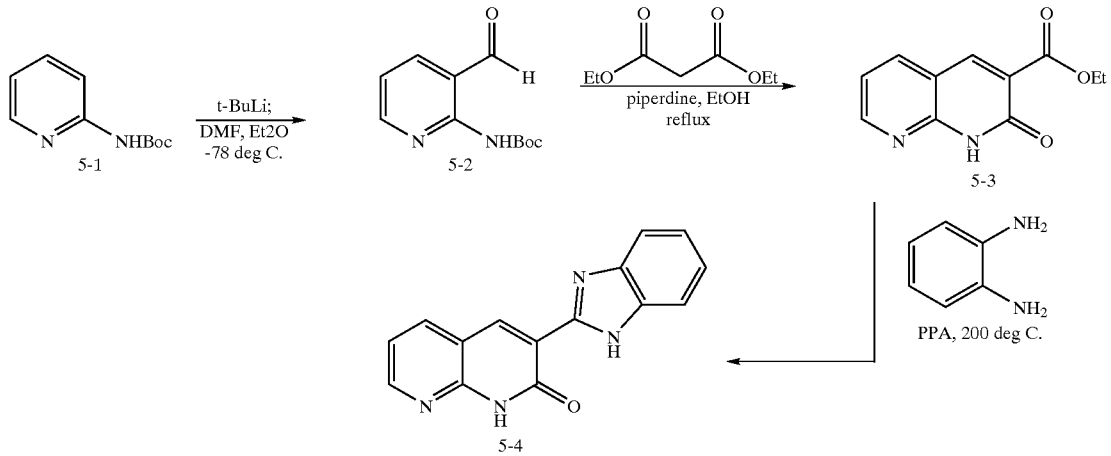

(3-Formyl-pyridin-2-yl)-carbamic Acid tert-Butyl Ester (5-2)

tert-Butyllithium (1.7 M, 14.5 mL, 24.6 mmol, 2.39 equiv) was added to a solution of pyridin-2-yl-carbamic acid tert-butyl ester (5-1, 2.00 g, 10.3 mmol, 1 equiv) in ethyl ether (100 mL) at −78° C., and the resulting mixture was warmed to 0° C. and stirred for 1 h. N,N-Dimethylformamide (8.00 mL, 103 mmol, 10.0 equiv) was added with rapid stirring. The mixture was stirred at 0° C. for 10 min, then partitioned between half-saturated aqueous ammonium chloride solution (100 mL). The aqueous layer was further extracted with ethyl acetate (100 mL), and the combined organic layers were dried over sodium sulfate and concentrated. The residue was purified by flash column chromatography (40% ethyl acetate in hexanes) to afford (3-formyl-pyridin-2-yl)-carbamic acid tert-butyl ester (5-2) as a white solid.

$^1$H NMR (300 MHz, CDCl$_3$) δ 10.18 (br s, 1H), 9.91 (s, 1H), 8.64 (dd, 1H, J=4.9, 2.9 Hz), 7.98 (dd, 1H, J=7.6, 2.0 Hz), 7.12 (dd, 1H, J=7.6, 4.9 Hz), 1.55 (s, 9H); TLC (40% EtOAc/hexanes), R$_f$=0.41.

2-oxo-1,2-Dihydro-[1,8]naphthyridine-3-carboxylic Acid Ethyl Ester (5-3):

A solution of 5-2 (1.53 g, 6.88 mmol, 1 equiv), diethyl malonate (2.09 mL, 13.8 mmol, 2.00 equiv), and piperidine (0.340 mL, 3.44 mmol, 0.500 equiv) in ethanol (20 mL) was heated at reflux for 16 h. The reaction mixture was allowed to cool to 23° C. The white crystals which formed were filtered and washed with ethanol (20 mL) to give 2-oxo-1,2-dihydro-[1,8]naphthyridine-3-carboxylic acid ethyl ester (5-3). $^1$H NMR (400 MHz, CDCl$_3$) δ 11.9 (br s, 1H), 8.85 (dd, 1H, J=4.8, 1.7 Hz), 8.46 (s, 1H), 8.03 (dd, 1H, J=7.9, 1.6 Hz), 7.27 (dd, 1H, J=7.9, 4.8 Hz), 4.45 (q, 2H, J=7.1 Hz), 1.43 (t, 3H, J=7.1 Hz).

3-(1H-Benzoimidazol-2-yl)-1H-[1,8]naphthyridin-2-one (5-4)

A mixture of 5-3 (300 mg, 1.37 mmol, 1 equiv) and 1,2-phenylenediamine (223 mg, 2.06 mmol, 1.5 equiv) in polyphosphoric acid (8 mL) was heated at 200° C. for 16 h. The hot rxn mixture was poured into ice water (50 mL), and the resulting mixture was allowed to stand until all polyphosphoric acid had dissolved. The acidic suspension was neutralized with saturated aqueous sodium bicarbonate solution, then extracted with ethyl acetate (5×100 mL). The combined organic layers were dried over sodium sulfate and concentrated. The residue was suspended in ethyl acetate (50 mL) aided by sonication, and the solids were filtered to give 3-(1H-benzoimidazol-2-yl)-1H-[1,8]naphthyridin-2-one (5-4) as a yellow solid.

$^1$H NMR (300 MHz, (CD$_3$)$_2$SO) δ 12.83 (br s, 1H), 12.64 (br s, 1H), 9.13 (s, 1H), 8.63 (dd, 1H, J=4.7, 1.8 Hz), 8.41 (dd, 1H, J=7.9, 1.8 Hz), 7.73 (m, 1H), 7.66 (m, 1H, 7.37 (dd, 1H, J=7.6, 4.7), 7.22 (m, 2H); HRMS (electrospray FT/ICR) calculated for C$_{15}$H$_{11}$N$_4$O [M+H]$^+$ 263.0927, found 263.0941.

SCHEME 6

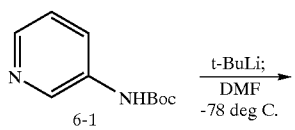

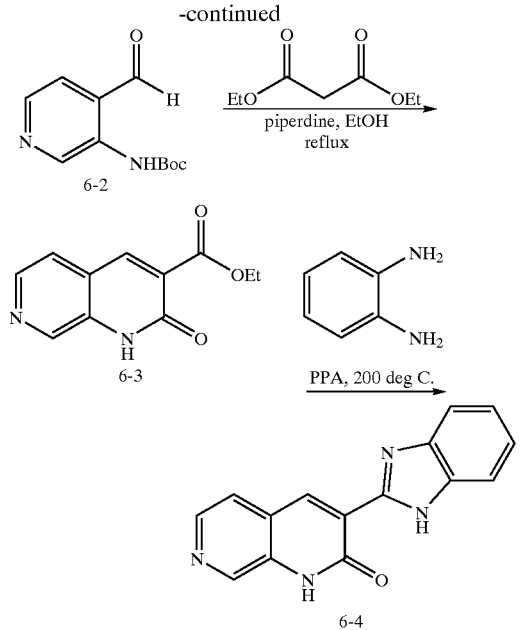

4-Formyl-pyridin-3-yl)-carbamic Acid tert-Butyl Ester (6-2)

tert-Butyllithium (1.7 M, 14.5 mL, 24.6 mmol, 2.39 equiv) was added to a solution of pyridin-3-yl-carbamic acid tert-butyl ester (6-1, 4.00 g, 20.6 mmol, 1 equiv) in THF (100 mL) at −78° C., and the resulting mixture stirred for 1 h. N,N-dimethylformamide (8.00 mL, 103 mmol, 5 equiv) was added, and the reaction mixture was warmed to 0° C. and stirred for 30 min. The mixture was partitioned between water (400 mL) and ethyl acetate (3×150 mL). The combined organic layers were dried over sodium sulfate and concentrated. The residue was purified by flash column chromatography (20% ethyl acetate in hexanes, grading to 40% ethyl acetate in hexanes) to afford (4-formyl-pyridin-3-yl)-carbamic acid tert-butyl ester (6-2) as a light yellow oil. $^1$H NMR (400 MHz, CDCl$_3$) δ 10.00 (s, 1H), 9.89 (br s, 1H), 9.84 (s, 1H), 8.53 (d, 1H, J=4.8 Hz), 7.49 (d, 1H, J=4.8 Hz), 1.55 (s, 9H); TLC (EtOAc), R$_f$=0.47.

2-oxo-1,2-Dihydro-[1,7]naphthyridine-3-carboxylic Acid Ethyl Ester (6-3)

A solution of 6-2 (2.20 g, 9.90 mmol, 1 equiv), diethyl malonate (3.00 mL, 19.8 mmol, 2.00 equiv), and piperidine (0.490 mL, 4.95 mmol, 0.500 equiv) in ethanol (50 mL) was heated at reflux for 20 h. The reaction mixture was allowed to cool to 23° C., then concentrated to about half its volume. The white crystals which formed were filtered and washed with cold ethanol (20 mL) to give 2-oxo-1,2-dihydro-[1,7]naphthyridine-3-carboxylic acid ethyl ester (6-3). $^1$H NMR (400 MHz, CDCl$_3$) δ 12.15 (br s, 1H), 8.94 (s, 1H), 8.52 (d, 1H, J=5.2 Hz), 8.46 (s, 1H), 7.52 (d, 1H, J=5.2 Hz), 4.48 (q, 2H, J=7.1 Hz), 1.46 (t, 3H, J=7.1 Hz); TLC (EtOAc), R$_f$=0.13.

3-(1H-Benzoimidazol-2-yl)-1H-[1,7]naphthyridin-2-one (6-4)

A mixture of 6-3 (300 mg, 1.37 mmol, 1 equiv) and 1,2-phenylenediamine (223 mg, 2.06 mmol, 1.5 equiv) in polyphosphoric acid (8 mL) was heated at 200° C. for 3 h. The hot rxn mixture was poured into ice water (50 mL), and the resulting mixture was allowed to stand until all polyphosphoric acid had dissolved. The acidic suspension was neutralized with saturated aqueous sodium bicarbonate solution, then extracted with ethyl acetate (5×100 mL). The combined organic layers were dried over sodium sulfate and concentrated. The residue was purified by flash column chromatography (EtOAc) to afford 3-(1H-benzoimidazol-2-yl)-1H-[1,7]naphthyridine-2-one (6-4) as a yellow solid. $^1$H NMR (400 MHz, (CD$_3$)$_2$SO) δ 12.75 (s, 1H), 12.71 (s, 1H), 9.13 (s, 1H), 8.79 (s, 1H), 8.43 (d, 1H, J=5.2 Hz), 7.91 (d, 1H, J=5.2 Hz), 7.74 (m, 1H), 7.68 (m, 1H), 7.24 (m, 2H). HRMS (electrospray FT/ICR) calculated for C$_{15}$H$_{11}$N$_4$O [M+H]$^+$ 263.0933, found 263.0930.

6-Chloro-2-oxo-1,2-dihydro-quinoline-3-carboxylic Acid Ethyl Ester (7-2)

A mixture of 4-chloro-2-nitrobenzaldehyde (7-1, 3.00 g, 16.0 mmol, 1 equiv) and 10% palladium on carbon (0.850 g, 0.800 mmol, 0.05 equiv) in ethanol (50 mL) was stirred under a hydrogen balloon for 2 h at 23° C. The catalyst was filtered onto a pad of celite and washed with ethanol (50 mL). The combined filtrate was concentrated to 20 mL, then diethyl malonate (3.92 mL, 25.8 mmol, 1.61 equiv) and piperidine (0.638 mL, 6.45 mmol, 0.403 equiv) were added. The resulting mixture was heated at reflux for 48 h. The mixture was allowed to cool to 23° C., and the precipitate was filtered and washed with cold ethanol (30 mL) to give 6-chloro-2-oxo-1,2-dihydro-quinoline-3-carboxylic acid ethyl ester (7-2) as a light yellow solid.

$^1$H NMR (300 MHz, (CD$_3$)$_2$SO) δ 8.46 (s, 1H), 7.96 (d, 1H, J=2.4 Hz), 7.64 (dd, 1H, J=8.8, 2.4 Hz), 7.33 (d, 1H, J=8.8 Hz), 4.28 (q, 2H, J=7.1 Hz), 1.30 (t, 3H, J=7.1 Hz).

3-(Benzoimidazol-2-yl)-6-chloro-quinolin-2-one (7-3)

A mixture of 6-chloro-2-oxo-1,2-dihydro-quinoline-3-carboxylic acid ethyl ester (7-2, 43 mg, 0.17 mmol, 1 equiv) and 1,2-phenylenediamine (37 mg, 0.34 mmol, 2.0 equiv) in polyphosphoric acid (3 mL) was heated at 200° C. for 2.5 h. The hot reaction mixture was poured into ice water (20 mL), and the resulting mixture was allowed to stand until all polyphosphoric acid had dissolved. The acidic suspension was neutralized with saturated aqueous sodium bicarbonate solution, then extracted with ethyl acetate (50 mL). The organic layer were dried over sodium sulfate and concentrated. The residue was suspended in ethyl ether (50 mL) aided by sonication, and the solids were filtered to give 3-(benzoimidazol-2-yl)-6-chloro-quinolin-2-one (7-3) as a yellow solid. $^1$H NMR (400 MHz, (CD$_3$)$_2$SO) δ 12.66 (br s, 1H), 12.58 (br s, 1H), 9.11 (s, 1H), 8.11 (d, 1H, J=2.2 Hz), 7.73 (m, 1H), 7.66 (m, 1H), 7.65 (dd, 1H, J=8.8, 2.4 Hz), 7.44 (d, 1H, J=8.8 Hz), 7.22 (m, 2H); HRMS (electrospray FT/ICR) calculated for C$_{16}$H$_{11}$N$_3$O [M+H]$^+$ 296.0591, found 296.0602.

SCHEME 7

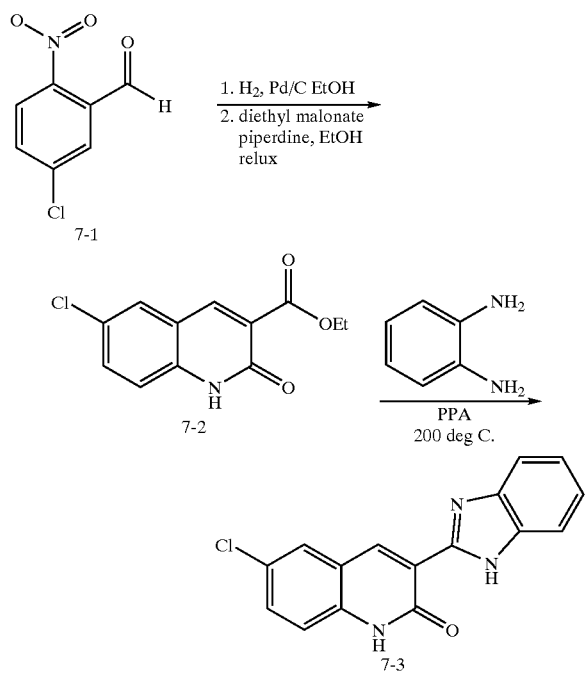

SCHEME 8

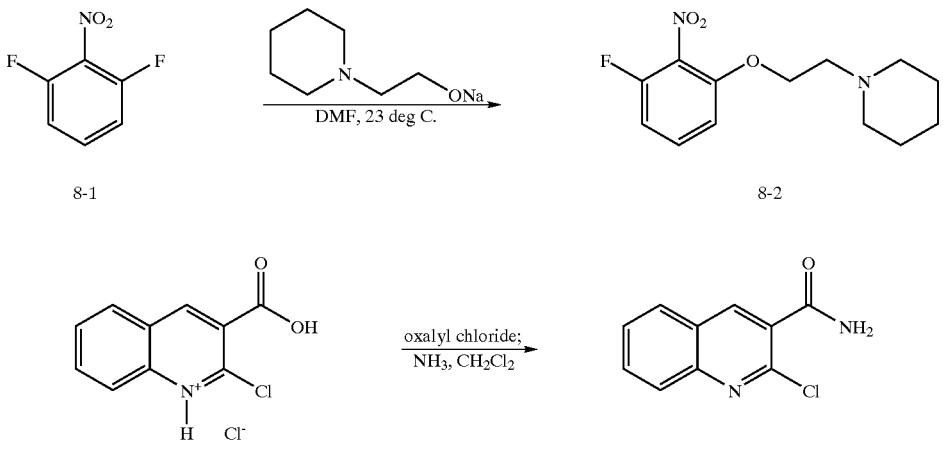

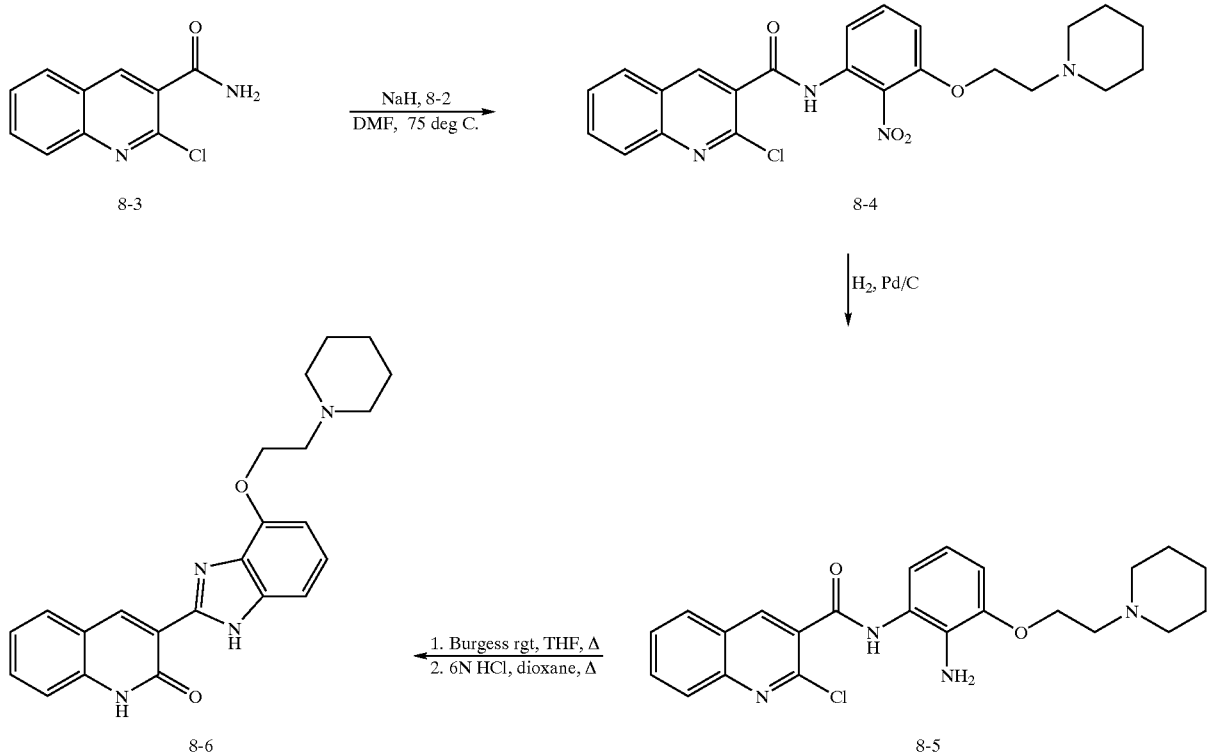

Synthesis of 8-2:

Sodium hydride (95%, 141 mg, 5.59 mmol. 1.00 equiv) and 2,6-difluoronitrobenzene (8-1, 900 mg, 5.59 mmol, 1.00 equiv) were added sequentially to a solution 1-(2-hydroxyethyl)piperidine (0.742 mL, 5.59 mmol, 1 equiv) in DMF (10 mL) at 0° C. The resulting mixture was warmed to 23° C. and stirred for 16 h. The mixture was partitioned between water (300 mL) and ethyl acetate (3×100 mL). The combined organic layers were dried over sodium sulfate and concentrated. The residue was purified by flash column chromatography ($CH_2Cl_2$ initially, grading to 5% MeOH in $CH_2Cl_2$) to give 8-2 as a light yellow oil. $^1$H NMR (400 MHz, $CDCl_3$) δ 7.38 (ddd, 1H, J=14.8, 8.6, 6.2 Hz), 6.83 (m, 2H), 4.22 (t, 2H, J=6.0 Hz), 2.78 (t, 2H, J=6.0), 2.48 (m, 4H), 1.58 (m, 4H), 1.44 (m, 2H).

Synthesis of 8-3:

Oxalyl chloride (1.58 mL, 18.1 mmol, 5.00 equiv) and N,N-dimethylformamide (10 μL, cat.) were added sequentially to a suspension of 2-4 (750 mg, 3.61 mmol, 1 equiv) in dichloromethane (50 mL) at 23° C., and the resulting mixture was stirred for 1 h. The homogeneous mixture was concentrated and the residue dissolved in dichloromethane (50 mL). Ammonia gas was passed through this solution for approximately 1 min. The cloudy mixture was partitioned between water (50 mL) and dichloromethane (50 mL), and the organic layer was dried over sodium sulfate and concentrated. The residue was suspended in a 1:1 mixture of ethyl ether sand hexane, and the solids were filtered to give 8-3 as a white solid. $^1$H NMR (400 MHz, $CDCl_3$) δ 8.75 (s, 1H), 8.06 (d, 1H, J=8.6 Hz), 7.92 (d, 1H, J=8.1 Hz), 7.84 (t, 1H, J=7.0 Hz), 7.64 (t, 1H, J=7.2 Hz), 6.72 (br s, 1H), 6.07 (br s, 1H).

Synthesis of 8-4:

Sodium hydride (95%, 19 mg, 0.74 mmol, 1.0 equiv) and a solution of 8-2 (200 mg, 0.740, 1 equiv) in DMF (2 mL) were sequentially added to a solution of 8-3 (153 mg, 0.740 mmol, 1.0 equiv) in DMF (2 mL) at 23° C. The resulting mixture was heated to 75° C. for 16 h. The reaction mixture was partitioned between water (200 mL) and ethyl acetate (2×100 mL). The combined organic layers were dried over sodium sulfate and concentrated. The residue was purified by flash column chromatography ($CHCl_3$ saturated with $NH_3$ initially, grading to 5% MeOH in $CHCl_3$ saturated with $NH_3$) to give 8-4 as a colorless oil. $^1$H NMR (400 MHz, $CDCl_3$) δ 9.18 (br s, 1H), 8.62 (s, 1H), 8.08 (d, 1H, J=8.8 Hz), 8.03 (br d, 1H, J=7.8 Hz), 7.94 (d, 1H, J=8.7 Hz), 7.86 (td, 1H, J=7.3, 1.5 Hz), 7.66 (td, 1H, J=7.3, 1.5 Hz), 7.52 (t, 1H, J=8.3 Hz), 6.92 (dd, 1H, J=8.6, 1.0 Hz), 4.25 (t, 2H, J=6.0 Hz), 2.70 (t, 2H, J=6.0 Hz), 2.49 (m, 4H), 1.59 (m, 4H), 1.43 (m, 2H).

Synthesis of 8-5:

A mixture of 8-4 (60 mg, 0.13 mmol, 1 equiv) and 10% palladium on carbon (140 mg, 0.13 mmol, 1.0 equiv) in ethyl acetate (30 mL) was stirred under a hydrogen balloon at 23° C. for 1 h. The catalyst was filtered onto a pad of celite and washed with ethyl acetate (30 mL). The combined filtrate was concentrated, and the residue purified by flash column chromatography ($CHCl_3$ sat'd with $NH_3$) to give 8-5 as a colorless oil. $^1$H NMR (400 MHz, $CDCl_3$) δ 8.62 (s, 1H), 8.33 (br s, 1H), 8.05 (d, 1H, J=8.4 Hz), 7.89 (d, 1H, J=8.0 Hz), 7.83 (t, 1H, J=7.3 Hz), 7.63 (t, 1H, J=7.3 Hz), 7.12 (dd, 1H, J=7.7, 1.0 Hz), 6.78 (t, 1H, J=8.0 Hz), 6.74 (br d, 1H, J=7.0 Hz), 4.21 (br s, 2H), 4.10 (t, 2H, J=5.8 Hz), 2.76 (t, 2H, J=5.8 Hz), 2.51 (m, 4H), 1.61 (m, 4H), 1.46 (m, 2H).

3-[4-(2-Piperidin-1-yl-ethoxy)-benzimidazol-2-yl]-quinolin-2-one (8-6):

(Methoxycarbonylsulfamoyl)triethylammonium hydroxide, inner salt, (Burgess rgt, 50 mg, 0.21 mmol, 3.0 equiv) was added to a solution of 8-5 (30 mg, 0.071 mmol, 1 equiv) in THF (4 mL) at reflux, and the resulting mixture was heated at reflux for 10 min. Additional Burgess reagent (50 mg, 0.21 mmol, 3.0 equiv) was added and heating was continued for 20 minutes. The reaction mixture was cooled to 23° C., then partitioned between water (40 mL) and ethyl acetate (2×40 mL). The aqueous layer was further extracted with dichloromethane (40 mL), then the combined organic layers were dried over sodium sulfate and concentrated. The residue was dissolved in a 1:1 mixture (5 mL) of dioxane and aqueous 6 N hydrochloric acid solution, and the resulting solution was heated at reflux for 1 h. The reaction mixture was cooled to 23° C., then partitioned between aqueous IN sodium hydroxide solution (30 mL) and $CH_2Cl_2$ (2×30 mL). The combined organic layers were dried over sodium sulfate and concentrated. The residue was purified by flash column chromatography ($CHCl_3$ saturated with $NH_3$ initially, grading to 3% MeOH in $CHCl_3$ saturated with $NH_3$) to give 8-6 as a yellow solid. $^1$H NMR (400 MHz, $CDCl_3$, major rotational isomer) δ 11.99 (br s, 1H), 9.57 (br s, 1H), 9.26 (s, 1H), 7.83 (d, 1H, J=7.9 Hz), 7.58 (td, 1H, J=7.3, 1.2 Hz), 7.35–7.14 (m, 4H), 6.73 (d, 1H, J=7.6 Hz), 4.39 (t, 2H, J=6.4 Hz), 2.97 (t, 2H, J=6.4 Hz), 2.58 (m, 4H), 1.64 (m, 4H), 1.48 (m, 2H). HRMS (electrospray FT/ICR) calculated for $C_{23}H_{25}N_4O_2$ $[M+H]^+$ 389.1978, found 389.1979.

3-(Benzoimidazol-2-yl)-7-chloro-quinolin-2-one (9-3)

A mixture of 9-2 (30 mg, 0.12 mmol, 1 equiv) and 1,2-phenylenediamine (39 mg, 0.36 mmol, 3.0 equiv) in polyphosphoric acid (3 mL) was heated at 200° C. for 3 h. The hot reaction mixture was poured into ice water (20 mL), and the resulting mixture was allowed to stand until all polyphosphoric acid had dissolved. The acidic suspension was neutralized with saturated aqueous sodium bicarbonate solution, then extracted with ethyl acetate (2×50 mL). The organic layer was dried over sodium sulfate and concentrated. The residue was suspended in ethyl ether (50 mL) aided by sonication, and the solids were filtered to afford 3-(benzoimidazol-2-yl)-7-chloro-quinolin-2-one (9-3) as a yellow solid. $^1$H NMR (400 MHz, $(CD_3)_2SO$) δ 12.63 (br s, 1H), 12.53 (br s, 1H), 9.13 (s, 1H), 8.01 (d, 1H, J=8.5 Hz), 7.72 (m, 1H), 7.65 (m, 1H), 7.22 (br s, 1H), 7.35 (dd, 1H, J=8.5, 1.9 Hz), 7.21 (m, 2H); HRMS (electrospray FT/ICR) calculated for $C_{16}H_{11}N_3O$ $[M+H]^+$ 296.0585, found 296.0590.

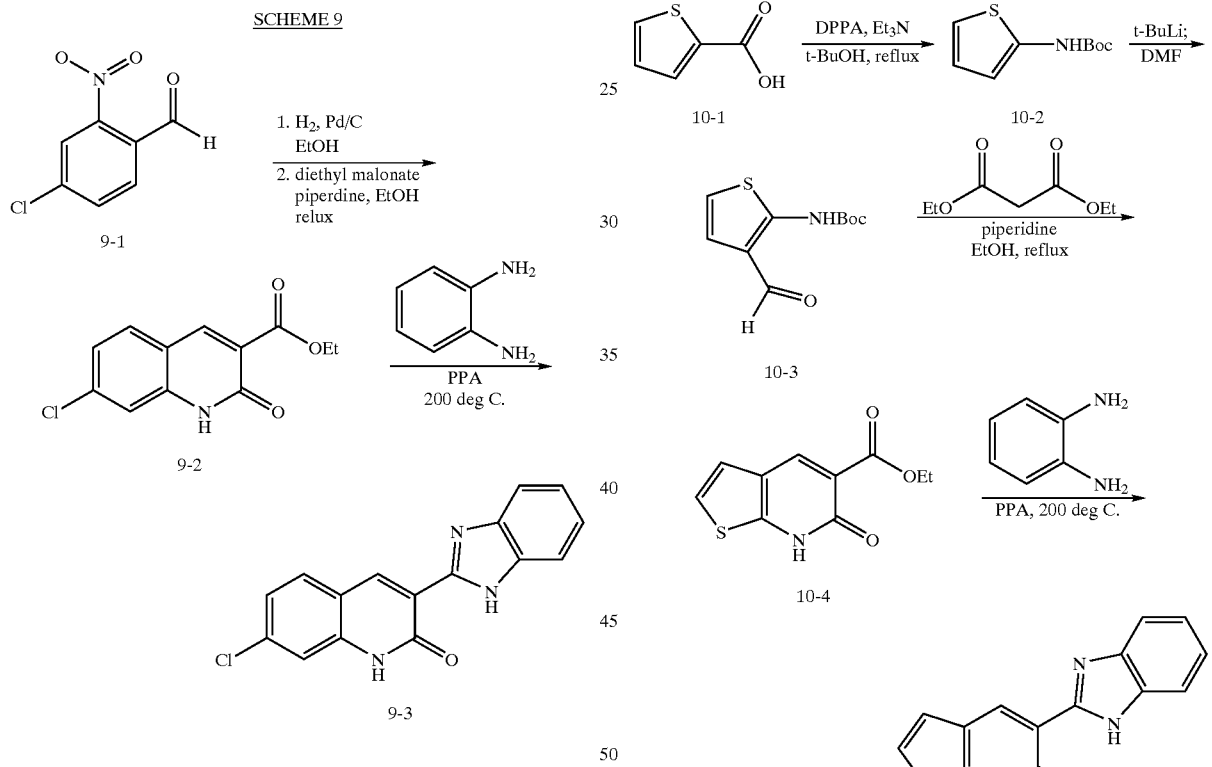

7-Chloro-2-oxo-1,2-dihydro-quinoline-3-carboxylic Acid Ethyl Ester (9-2)

A mixture of 4-chloro-2-nitrobenzaldehyde (9-1, 495 mg, 2.64 mmol, 1 equiv) and 10% palladium on carbon (0.280 g, 0.264 mmol, 0.100 equiv) in ethanol (20 mL) was stirred under a hydrogen balloon for 1 h at 23° C. The catalyst was filtered onto a pad of celite and washed with ethanol (20 mL). The combined filtrate was concentrated to 20 mL, then diethyl malonate (0.801 mL, 5.28 mmol, 2.00 equiv) and piperidine (0.130 mL, 1.32 mmol, 0.500 equiv) were added. The resulting mixture was heated at reflux for 5 h. The mixture was allowed to cool to 23° C., and the precipitate was filtered and washed with cold ethanol (10 mL) to give 7-chloro-2-oxo-1,2-dihydro-quinoline-3-carboxylic acid ethyl ester (9-2) as a white solid.

$^1$H NMR (400 MHz, $(CDCl_3)$ δ 8.53 (s, 1H), 7.60 (d, 1H, J=8.4 Hz), 7.42 (d, 1H, J=1.5 Hz), 7.23 (dd, 1H, J=8.4, 1.8 Hz), 4.46 (q, 2H, J=7.1 Hz), 1.46 (t, 3H, J=7.1 Hz).

tert-Butyl 2-Thienylcarbamate (10-2)

A solution of 2-thiophenecarboxylic acid (10-1, 10.0 g, 78.0 mmol, 1 equiv), diphenyiphosphoryl azide (20.2 mL, 93.6 mmol, 1.20 equiv) and triethylamnine (17.4 mL, 125 mmol, 1.60 equiv) in t-BuOH (200 mL) was heated at reflux for 60 h. The reaction mixture was cooled, then concentrated. The residue was partitioned between saturated aqueous sodium bicarbonate solution and EtOAc (2×200 mL). The combined organic layers were dried over sodium sulfate, then concentrated. The residue was suspended in a 4:1 mixture of hexane and ethyl ether, and the resulting solid was filtered and air-dried to give tert-butyl 2-thienylcarbamate (10-2). $^1$H NMR (300 MHz, CDCl$_3$) δ 6.96 (s, 1 H), 6.81 (m, 2H), 6.52 (dd, 1H, J=3.4, 1.9 Hz), 1.55 (s, 9H).

tert-Butyl 3-Formyl-2-thienylcarbamate (10-3)

A solution of tert-butyllithium in pentane (1.7 M, 35.4 mL, 60.2 mmol, 2.40 equiv) was added to a solution of tert-butyl 2-thienylcarbamate (10-2, 5.00 g, 25.1 mmol, 1 equiv) in THF (75 mL) at −78° C., and the resulting mixture was stirred at −78° C. for 1.5 h. N,N-Dimethylformamide (5.83 mL, 75.3 mmol, 3.00 equiv) was added, and the mixture was then warmed to 0° C. The reaction mixture was partitioned between water (300 mL) and EtOAc (2×200 mL). The combined organic layers were then dried over sodium sulfate and concentrated, and the residue was purified by flash column chromatography (hexane, initially, grading to 30% hexane in EtOAc) to give tert-butyl 3-formyl-2-thienylcarbamate (10-3) as a colorless oil. $^1$H NMR (400 MHz, CDCl$_3$) δ 10.51 (s, 1H), 9.80 (s, 1H), 7.11 (d, 1H, J=5.7 Hz), 6.68 (d, 1H, J=5.9 Hz), 1.55 (s, 9H).

Ethyl 6-oxo-6,7-Dihydrothieno[2,3-b]pyridine-5-carboxylate (10-4)

A solution of tert-butyl 3-formyl-2-thienylcarbamate (11-3, 1.90, 8.36 mmol, 1 equiv), diethyl malonate (2.54 mL, 16.7 mmol, 2.00 equiv), and piperidine (0.413 mL, 4.18 mmol, 0.500 equiv) in EtOH (100 mL) was heated at reflux for 6 h. The reaction mixture was concentrated, and the residue was purified by flash column chromatography (EtOAc, initally, then 10% MeOH in EtOAc) to give ethyl 6-oxo-6,7-dihydrothieno[2,3-b]pyridine-5-carboxylate (10-4). $^1$H NMR (400 MHz, CDCl$_3$) δ 11.57 (brs, 1H), 8.60 (s, 1H), 7.33 (d, 1H, J=6.0 Hz), 7.21 (d, 1H, J=6.0 Hz), 4.49 (q, 2H, J=7.1 Hz), 1.46 (t, 3H, J=7.1 Hz).

5-(1H-Benzimidazol-2-yl)thieno[2,3-b]pyridin-6(7H)-one (10-5)

A mixture of ethyl 6-oxo-6,7-dihydrothieno[2,3-b]pyridine-5-carboxylate (11-4, 100 mg, 0.448 mmol, 1 equiv) and 1,2-phenylenediamine (97 mg, 0.90 mmol, 2.0 equiv) was heated in polyphosphoric acid (5 mL) at 200° C. for 2 h. The hot reaction mixture was poured into ice water. Once all the residual polyphosphoric acid had dissolved, the aqueous mixture was basified with saturated sodium carbonate solution, then extracted with EtOAc (2×100 mL). The combined organic layers were dried over sodium sulfate and concentrated. The residue was purified by reverse-phase liquid chromotography (H$_2$O/CH$_3$CN gradient w/0.1% TFA present) to provide 5-(1H-benzimidazol-2-yl)thieno[2,3-b]pyridin-6(7H)-one (10-5) as a TFA salt (yellow solid). $^1$H NMR (300 MHz, CD$_3$OD) δ 8.90 (s, 1H), 7.85 (m, 2H), 7.60 (m, 2H), 7.38 (d, 1H, J=5.9 Hz), 7.38 (d, 1H, J=5.9 Hz), 7.34 (d, 1H, J=6.1 Hz).

SCHEME 11

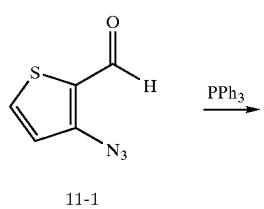

11-1

-continued

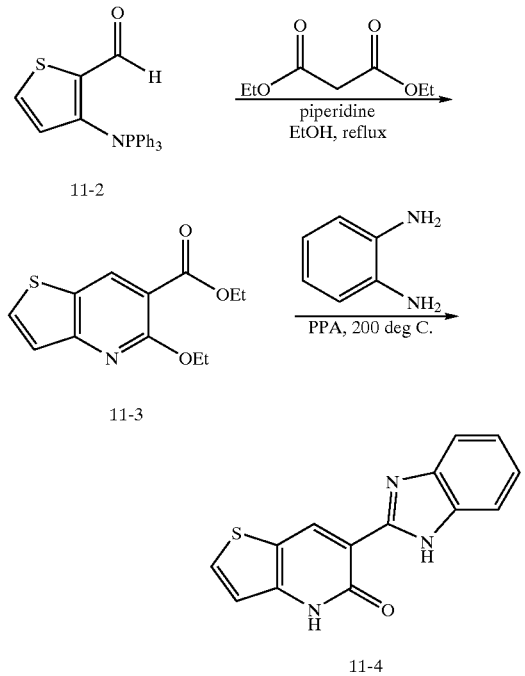

3-[(Triphenylphosphoranlidene)amino]-2-thiophenecarbaldehyde (11-2):

A solution of 3-azido-2-thiophenecarbaldehyde (11-1, 1.00 g, 6.53 mmol, 1 equiv, prepared by the method of Gronowitz, S., Westerlund, C., and Hornfeldt, A.-B. *Acta. Chem. Scand. B* 1975, 29, 224–232) and triphenylphosphine (1.71 g, 6.53 mmol, 1.00 equiv) in THF (30 mL) was stirred at 23° C. for 6 h. The reaction mixture was concentrated to give 3-[(triphenylphosphoranylidene)amino]-2-thiophenecarbaldehyde (11-2). $^1$H NMR (400 MHz, CD$_3$OD) δ 10.35 (s, 1H), 7.72 (m, 6H), 7.58 (m, 2H), 7.49 (m, 6H), 7.27 (dd, 1H, J=4.5, 0.8 Hz), 6.09 (d, 1H, J=4.5 Hz).

Ethyl 5-Ethoxythieno[3,2-b]pyridine-6-carboxylate (11-3)

A solution of 3-[(triphenylphosphoranylidene)amino]-2-thiophenecarbaldehyde (11-2, 2.50 g, 6.45 mmol, 1 equiv), diethyl malonate (1.96 mL, 12.9 mmol, 2.00 equiv), and piperidine (0.319 mL, 3.23 mmol, 0.500 equiv) in EtOH (50 mL) was heated at reflux for 16 h. The reaction mixture was concentrated, and the residue was purified by flash column chromatography (heaxane, initally, grading to 30% EtOAc in hexane) to give ethyl 5-ethoxythieno[3,2-b]pyridine-6-carboxylate (11-3) as an off-white solid. $^1$H NMR (300 MHz, CDCl$_3$) δ 8.64 (s, 1H), 7.84 (d, 1H, J=7.4 Hz), 7.37 (d, 1H, J=7.2 Hz), 4.55 (q, 2H, J=7.0 Hz), 4.40 (q, 2H, J=7.1 Hz), 1.48 (t, 3H, J=7.0 Hz), 1.41 (t, 3H, J=7.1 Hz).

6-(1H-Benzimidazol-2-yl)thieno[3,2-b]pyridin-5(4H)-one (11-4)

A mixture of ethyl 5-ethoxythieno[3,2-b]pyridine-6-carboxylate (11-3, 200 mg, 0.796 mmol, 1 equiv) and 1,2-phenylenediamine (172 mg, 1.59 mmol, 2.00 equiv) was heated in polyphosphoric acid (5 mL) at 200° C. for 3 h. The hot reaction mixture was poured into ice water. Once all the residual polyphosphoric acid had dissolved, the solid which had precipitated was filtered and air dried. The solid was then suspended in saturated sodium carbonate solution and extracted with hot EtOAc (2×200 mL). The combined organic layers were dried over sodium sulfate and concentrated. The residue was purified by reverse-phase liquid chromotography (H₂O/CH₃CN gradient w/0.1% TFA present) to provide 6-(1H-benzimidazol-2-yl)thieno[3,2-b]pyridin-5(4H)-one (11-4) as a TFA salt (yellow solid). ¹H NMR (400 MHz, CD₃OD) δ 8.99 (s, 1H), 8.25 (d, 1H, J=5.3 Hz), 7.83 (m, 2H), 7.58 (m, 2H), 7.21 (d, 1H, J=5.5 Hz).

tert-butyl 3-{[tert-butyl(dimethyl)silyl]oxy}phenyl carbamate (12-3, 5.00 g, 15.5 mmol, 1 equiv) in ethyl ether (150 mL) at −40° C., and the resulting mixture was stirred at −40° C. for 2 h. N,N-Dimethylformamide (9.57 mL, 124 mmol, 8.00 equiv) was added, and the mixture was then warmed to 0° C. The reaction mixture was partitioned between water (500 mL) and ethyl ether (500 mL). The organic layer was dried over sodium sulfate and concentrated, and the residue

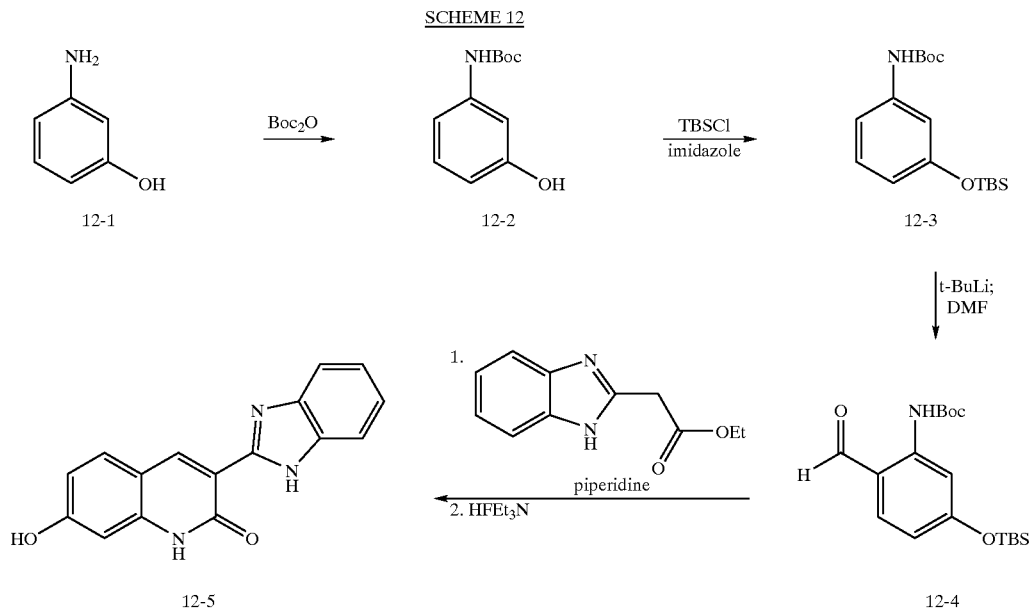

SCHEME 12 tert-Butyl 3-Hydroxyphenylcarbamate (12-2)

A solution of 3-aminophenol (5.00 g, 45.8 mmol, 1 equiv) and di-t-butyl dicarbonate (10.0, 45.8 mmol, 1.00 equiv) in t-BuOH (100 mL) was heated at reflux for 20 h. The reaction mixture was cooled and concentrated to give tert-butyl 3-hydroxyphenyl carbamate (12-2) as a colorless oil. ¹H NMR (400 MHz, CDCl₃) δ 7.13 (m, 2H), 6.74 (ddd, 1H, J=8.6, 2.0, 0.6 Hz), 6.52 (ddd, 1H, J=8.6, 2.0, 0.6 Hz), 6.44 (br s, 1H), 4.79 (s, 1H), 1.52 (s, 9H).

tert-Butyl 3-{[tert-Butyl(dimethyl)silyl]oxy}phenylcarbamate (12-3)

A solution of tert-butyl 3-hydroxyphenylcarbamate (12-2, 6.40 g, 30.6 mmol, 1 equiv), t-butyldimethylsilyl chloride (4.61 g, 30.6 mmol, 1.00 equiv), and imidazole (2.71 g, 39.8 mmol, 1.30 equiv) in DMF (50 mL) was stirred at 23° C. for 16 h. The reaction mixture was partitioned between half-saturated sodium bicarbonate solution and ethyl acetate (200 mL). The organic layer was washed successively with half-saturated ammonium chloride solution (100 mL), saturated sodium bicarbonate solution (100 mL), and brine (100 mL), then dried over sodium sulfate and concentrated to give tert-butyl 3-{[tert-butyl(dimethyl)silyl]oxy}phenylcarbamate (12-3) as a white solid. ¹H NMR (400 MHz, CDCl₃) δ 6.92 (t, 1H, J=7.8 Hz), 6.73 (m, 2H), 6.31 (ddd, 1H, J=7.8, 1.9, 0.7 Hz), 6.20 br s, 1H), 1.32 (s, 9H), 0.78 (s, 9H), −0.02 (s, 6H).

tert-Butyl 5-{[tert-Butyl(dimethyl)silyl]oxy}-2-formylphenylcarbamate (12-4)

A solution of tert-butyllithium in pentane (1.7 M, 21.8 mL, 37.1 mmol, 2.40 equiv) was added to a solution of was purified by flash column chromatography (hexane, initially, grading to 20% hexane in EtOAc) to give tert-butyl 5-{[tert-butyl(dimethyl)silyl]oxy}-2-formylphenylcarbamate (12-4) as a colorless oil. ¹H NMR (400 MHz, CDCl₃) δ 10.34 (s, 1H), 9.54 (s, 1H), 7.76 (d, 1H, J=1.8 Hz), 7.26 (d, 1H, J=7.8 Hz), 6.35 (dd, 1H, J=7.8, 1.9 Hz), 1.37 (s, 9H), 0.78 (s, 9H), −0.02 (s, 6H).

3-(1H-Benzimidazol-2-yl)-7-hydroxy-2(1H)-quinolinone (12-5)

A solution of tert-butyl 5-{[tert-butyl(dimethyl)silyl]oxy}-2-formylphenylcarbamate (12-4, 0.57 g, 2.4 mmol, 1 equiv), ethyl 1H-benzimidazol-2-ylacetate (0.50 g, 2.4 mmol, 1.0 equiv, prepared by the method of Rahmouni, M, Derdour, A., Bazureau, J., and Hamelin *Tetrahedron Lett.* 1994, 35, 4563–4564), and piperidine (0.12 mL, 1.2 mmol, 0.5 equiv) in ethanol (50 mL) was heated at reflux for 20 h. The reaction mixture was cooled and concentrated. A solution of the residue and triethylamine trihydrofluoride (0.38 mL, 2.3 mmol, 0.97 equiv) in acetonitrile (30 mL) was stirred at 30° C. for 2.5 h. The precipitate which formed was filtered and air dried to give 3-(1H-benzimidazol-2-yl)-7-hydroxy-2(1H)-quinolinone (12-5) as an off-white solid. ¹H NMR (400 MHz, DMSO-d₆) δ 12.51 (s, 1H), 12.19 (s, 1H), 10.45 (br s, 1H), 8.95 (s, 1H), 7.76 (d, 1H, J=8.8 Hz), 7.68 (m, 1H), 7.59 (m, 1H), 7.18 (m, 2H), 6.82 (s, 1H), 6.75 (d, 1H, J=8.8 Hz).

SCHEME 13

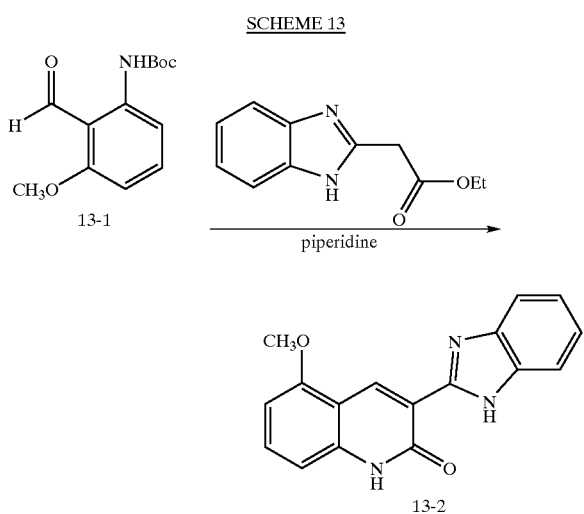

3-(1H-Benzimidazol-2-yl)-8-methoxy-2(1H)-quinolinone (13-2)

A solution of tert-butyl 2-formyl-3-methoxyphenylcarbamate (13-1, 0.50 g, 1.9 mmol, 1 equiv, prepared by the formylation method utilized in the examples above), ethyl 1H-benzimidazol-2-ylacetate (0.39 g, 1.9 mmol, 1.0 equiv, prepared by the method of Rahmouni, M, Derdour, A., Bazureau, J., and Hamelin *Tetrahedron Lett.* 1994, 35, 4563–4564), and piperidine (0.090 mL, 0.91 mmol, 0.48 equiv) in ethanol (50 mL) was heated at reflux for 20 h. The reaction mixture was cooled and the precipitate which formed was filtered and air dried to give 3-(1H-benzimidazol-2-yl)-8-methoxy-2(1H)-quinolinone (13-2). $^1$H NMR (400 MHz, DMSO-$d_6$) δ 12.59 (s, 1H), 12.43 (s, 1H), 9.25 (s, 1H), 7.71 (m, 1H), 7.66 (m, 1H), 7.55 (t, 1H, J=8.2 Hz), 7.20 (m, 2H), 7.03 (d, 1H, J=8.2 Hz), 6.85 (d, 1H, J=8.2 Hz).

SCHEME 14

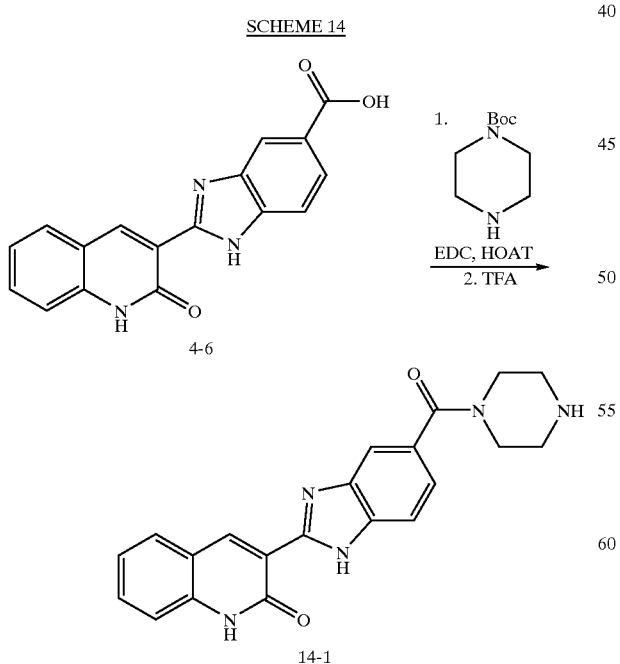

A mixture of 2-(2-oxo-1,2-dihydro-3-quinolinyl)-1H-benzimidazole-5-carboxylic acid (4-6, 130 mg, 0.43 mmol, 1 equiv, tert-butyl 1-piperazinecarboxylate (79 mg, 0.43 mmol, 1.0 equiv), 1-(3-dimethylaminopropyl)-3-ethylcarbodiimide hydrochloride (97 mg, 0.51 mmol, 1.2 equiv), 1-hydroxy-7-azabenzotriazole (70 mg, 0.51 mmol, 1.2 equiv), and triethylamine (0.148 mL, 1.06 mmol, 2.50 equiv) in DMF (5.0 mL) was stirred at 23° C. for 20 h. The reaction mixture was partitioned between water (50 mL) ethyl actate (3×50 mL). The combined organic layers were dried over sodium sulfate and concentrated. A solution of the residue, DMSO (10 uL), and water (10 uL) in a 1:1 mixture of dichloromethane and trifluoroacetic acid (20 mL) was stirred at 23° C. for 45 min. The reaction mixture was concentrated, and the residue was purified by reverse-phase liquid chromotography ($H_2O/CH_3CN$ gradient w/0.1% TFA present). The desired fractions were partitioned between saturated sodium bicarbonate solution (50 mL) and a 10% solution of methanol in dichloromethane (2×50 mL) to provide 3-[5-(1-piperazinylcarbonyl)-1H-benzimidazol-2-yl]-2(1H)-quinolinone (14-1) as its free base. $^1$H NMR (500 MHz, DMSO-$d_6$) δ 11.83 (s, 1H), 8.59 (s, 1H), 7.74 (m, 2H), 7.53 (m, 2H), 7.39 (m, 2H), 7.26 (m, 2H), 3.61 (br m, 1H), 3.60 (br m, 1H), 3.32 (br m, 1H), 1.98 (br m, 1H), 1.89 (br m, 1H), 1.62 (br m, 2H).

3-{5-[(4-Amino-1-piperidinyl)carbonyl]-1H-benzimidazol-2-yl}-2(1H)-quinolinone (14-2)

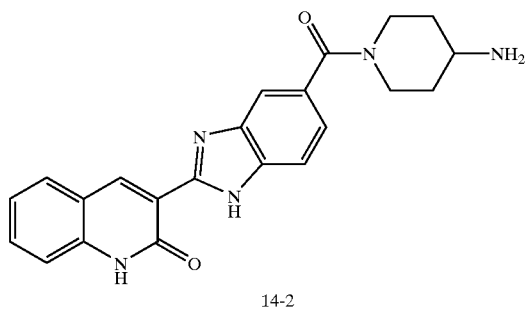

3-{5-[(4-amino-1-piperidinyl)carbonyl]-1H-benzimidazol-2-yl}-2(1H)-quinolinone was prepared by the same method used to prepare 14-1 above. $^1$H NMR (500 MHz, DMSO-$d_6$) δ 12.80 (br s, 1H), 9.14 (s, 1H), 7.97 (d, 1H, J=8.3 Hz), 7.75 (m, 1H), 7.64 (m, 2H), 7.45 (d, 1H, J=8.3 Hz), 7.31 (t, 1H, J=7.6 Hz), 7.22 (d, 1H, J=7.6 Hz), 3.70 (br m, 1H), 3.02 (br m, 2H), 2.89 (br m, 2H), 1.78 (br m, 2H), 1.24 (br m, 2H).

The following compounds may be synthesized via the protocols described above and modifications thereof. The requisite starting materials and reactions would be readily apparent to the skilled artisan.

| No. | Structure | Name |
|---|---|---|
| 15-1 | 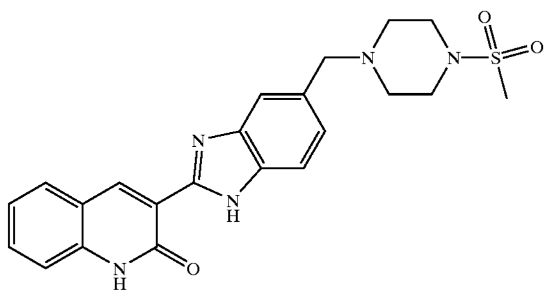 | 3-(5-{[4-(methylsulfonyl)-1-piperazinyl]methyl}-1H-benzimidazol-2-yl)-2(1H)-quinolinone |
| 15-2 | 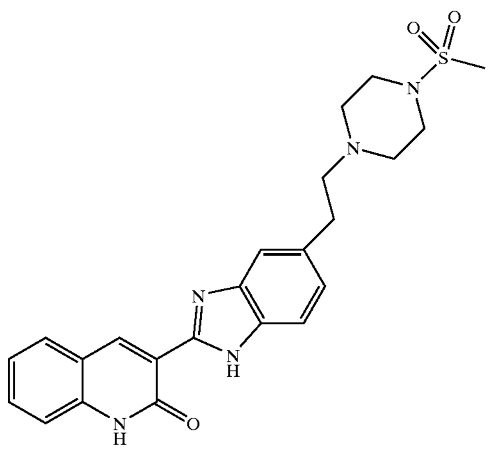 | 3-(5-{2-[4-(methylsulfonyl)-1-piperazinyl]ethyl}-1H-benzimidazol-2-yl)-2(1H)-quinolinone |
| 15-3 | 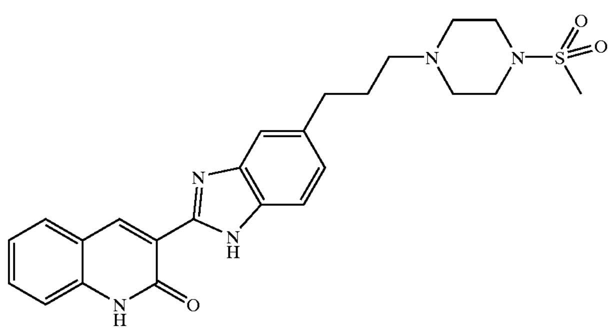 | 3-(5-{2-[4-(methylsulfonyl)-1-piperazinyl]propyl}-1H-benzimidazol-2-yl)-2(1H)-quinolinone |
| 15-4 | 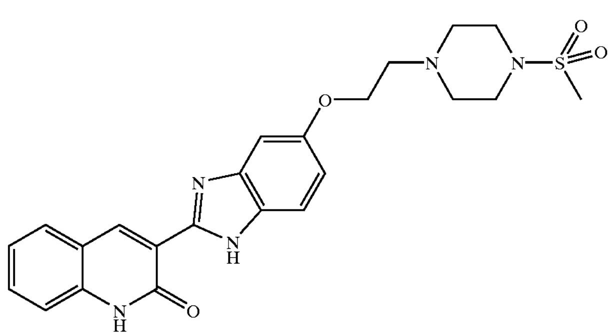 | 3-(5-{[4-(methylsulfonyl)-1-piperazinyl]ethoxy}-1H-benzimidazol-2-yl)-2(1H)-quinolinone |

-continued

| No. | Structure | Name |
|---|---|---|
| 15-5 | 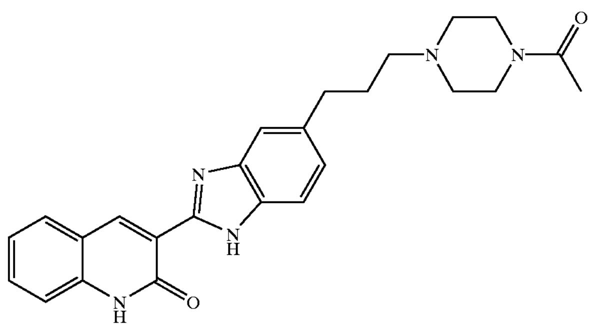 | 3-(5-{[4-acetyl-1-piperazinyl]methyl}-1H-benzimidazol-2-yl)-2(1H)-quinolinone |
| 15-6 | 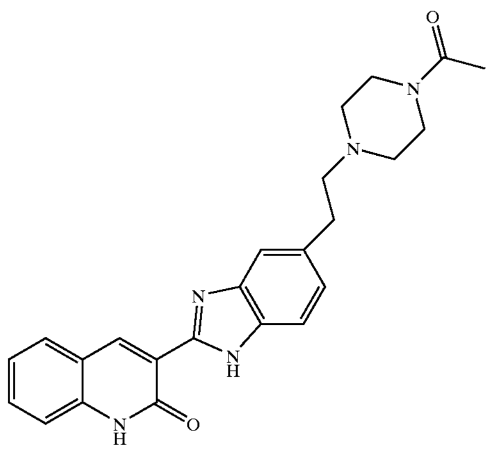 | 3-(5-{2-[4-acetyl-1-piperazinyl]ethyl}-1H-benzimidazol-2-yl)-2(1H)-quinolinone |
| 15-7 | 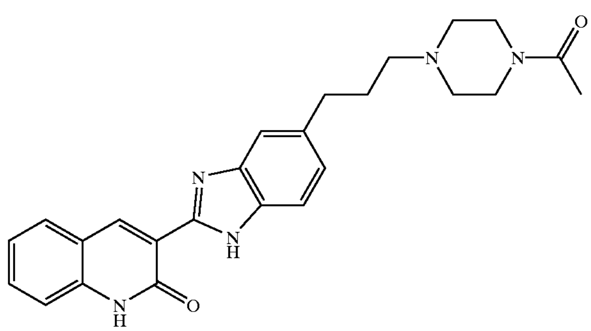 | 3-(5-{3-[4-acetyl-1-piperazinyl]propyl}-1H-benzimidazol-2-yl)-2(1H)-quinolinone |
| 15-8 | 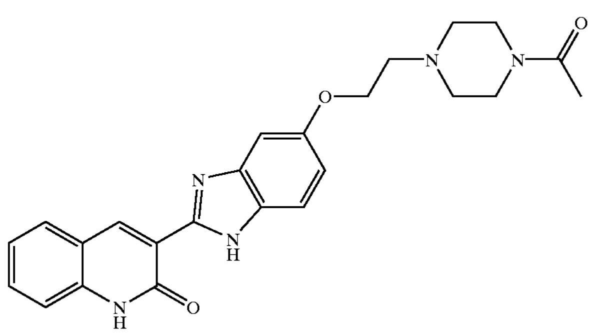 | 3-(5-{2-[4-acetyl-1-piperazinyl]ethoxy}-1H-benzimidazol-2-yl)-2(1H)-quinolinone |

-continued

| No. | Structure | Name |
|---|---|---|
| 15-9 | 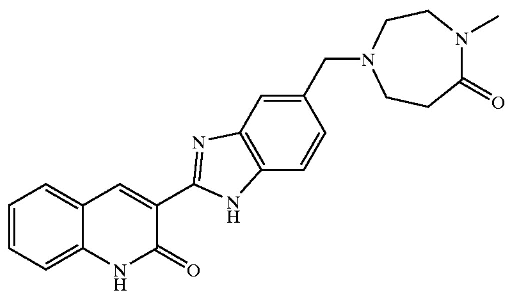 | 3-(5-{[4-methyl-5-oxo-1,4-diazepan-1-yl)methyl}-1H-benzimidazol-2-yl)-2(1H)-quinolinone |
| 15-10 | 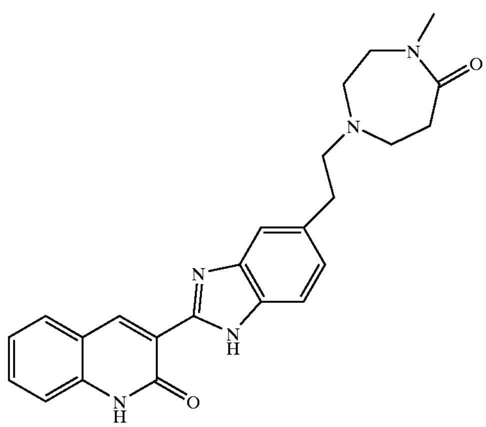 | 3-(5-{2-[4-methyl-5-oxo-1,4-diazepan-1-yl)ethyl}-1H-benzimidazol-2-yl)-2(1H)-quinolinone |
| 15-11 | 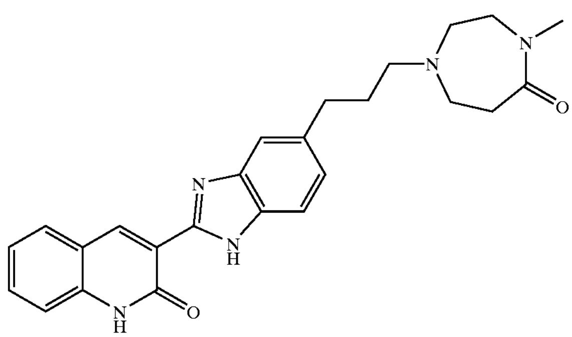 | 3-(5-{3-[4-methyl-5-oxo-1,4-diazepan-1-yl)propyl}-1H-benzimidazol-2-yl)-2(1H)-quinolinone |
| 15-12 | 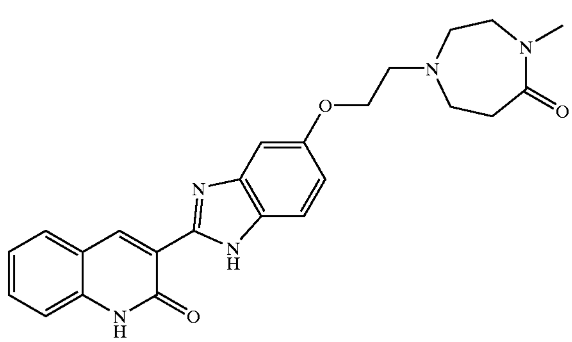 | 3-(5-{2-[4-methyl-5-oxo-1,4-diazepan-1-yl)ethoxy}-1H-benzimidazol-2-yl)-2(1H)-quinolinone |

| No. | Structure | Name |
|---|---|---|
| 15-13 | 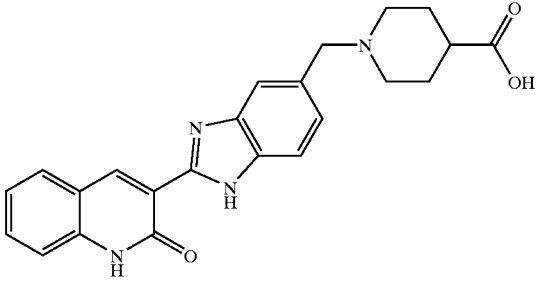 | 1-{[2-(2-oxo-1,2-dihydro-3-quinolinyl)-1H-benzimidazol-5-yl]methyl}-piperidine-4-carboxylic acid |
| 15-14 | 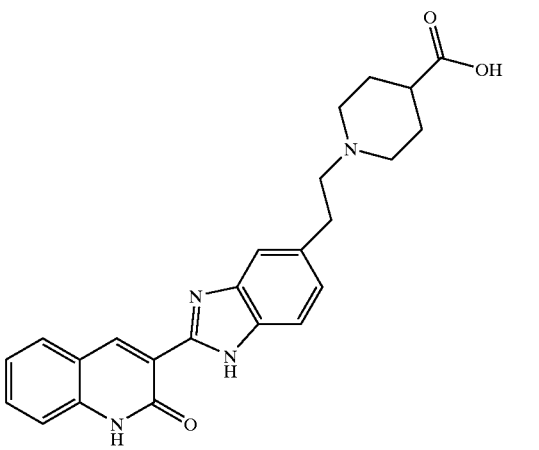 | 1-{2-[2-(2-oxo-1,2-dihydro-3-quinolinyl)-1H-benzimidazol-5-yl[ethyl}-piperidine-4-carboxylic acid |
| 15-15 | 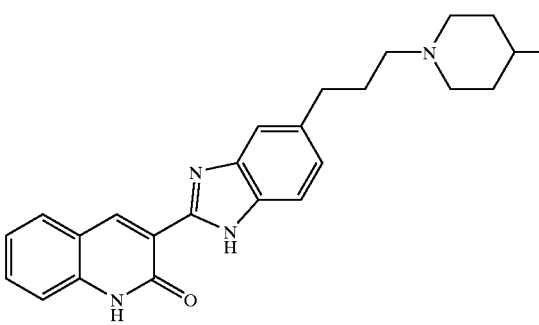 | 1-{2-[2-(2-oxo-1,2-dihydro-3-quinolinyl)-1H-benzimidazol-5-yl[propyl}-piperidine-4-carboxylic acid |
| 15-16 | 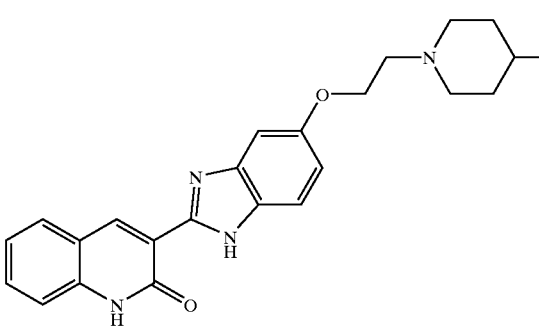 | 1-{2-[2-{2-oxo-1,2-dihydro-3-quinolinyl}-1H-benzimidazol-5-yl)oxy]-methyl}-piperidine-4-carboxylic acid |

-continued
| No. | Structure | Name |
|---|---|---|
| 15-17 | 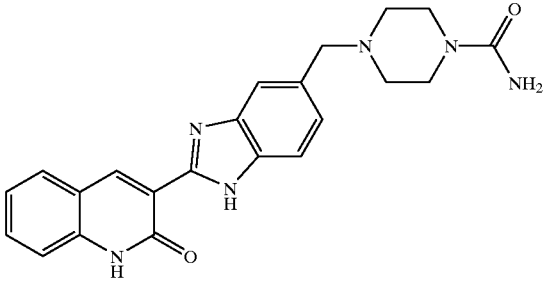 | 4-{[2-(2-oxo-1,2-dihydro-3-quinolinyl)-1H-benzimidazol-5-yl]-methyl}-piperazine-1-carboxamide |
| 15-18 | 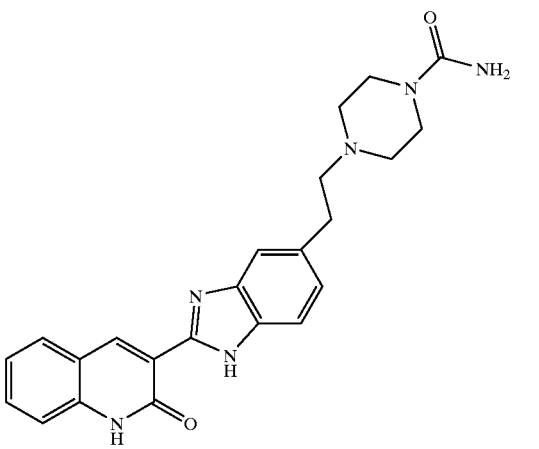 | 4-{2-[2-(2-oxo-1,2-dihydro-3-quinolinyl)-1H-benzimidazol-5-yl]ethyl}-piperazine-1-carboxamide |
| 15-19 | 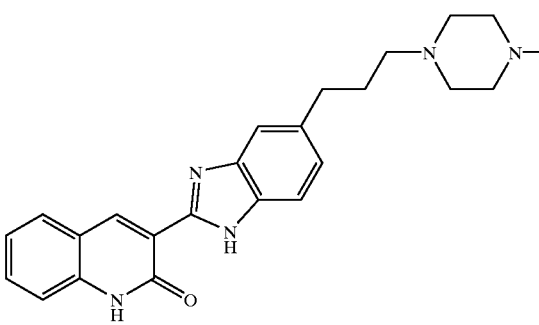 | 4-{3-[2-(2-oxo-1,2-dihydro-3-quinolinyl)-1H-benzimidazol-5-yl]propyl}-piperazine-1-carboxamide |
| 15-20 | 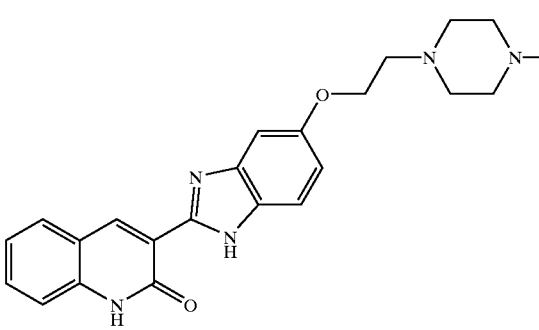 | 4-(2-{[2-(2-oxo-1,2-dihydro-3-quinolinyl)-1H-benzimidazol-5-yl]-oxy}-ethyl)-piperazine-1-carboxamide |

-continued

| No. | Structure | Name |
|---|---|---|
| 15-21 | 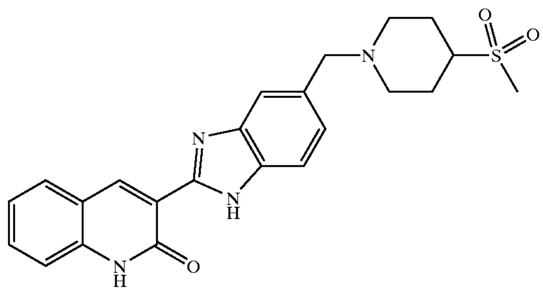 | 3-(5-{[4-(methylsulfonyl)-1-piperidinyl]methyl}-1H-benzimidazol-2-yl)-2(1H)-quinolinone |
| 15-22 | 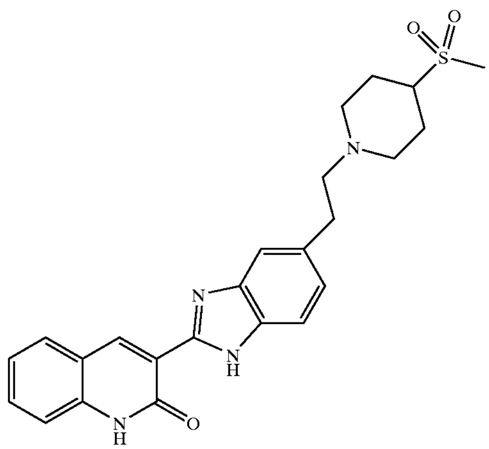 | 3-(5-{2-[4-(methylsulfonyl)-1-piperidinyl]-ethyl}-1H-benzimidazol-2-yl)-2(1H)-quinolinone |
| 15-23 | 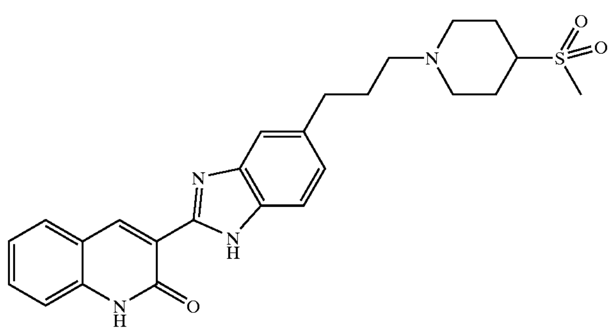 | 3-(5-{3-[4-(methylsulfonyl)-1-piperidinyl]-propyl}-1H-benzimidazol-2-yl)-2(1H)-quinolinone |
| 15-24 | 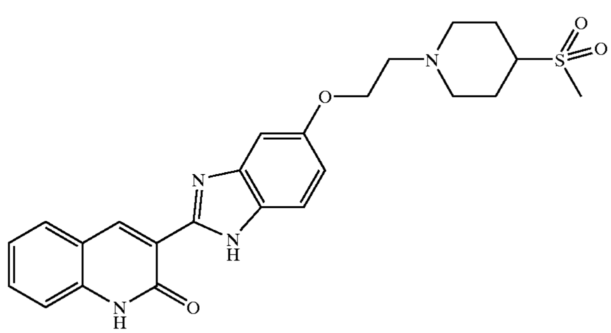 | 3-(5-{2-[4-(methylsulfonyl)-1-piperidinyl]-ethoxy}-1H-benzimidazol-2-yl)-2(1H)-quinolinone |

What is claimed is:

1. A compound of Formula I

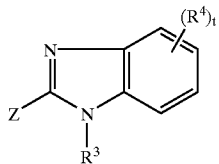

I or a pharmaceutically acceptable salt or stereoisomer thereof, wherein

Z is

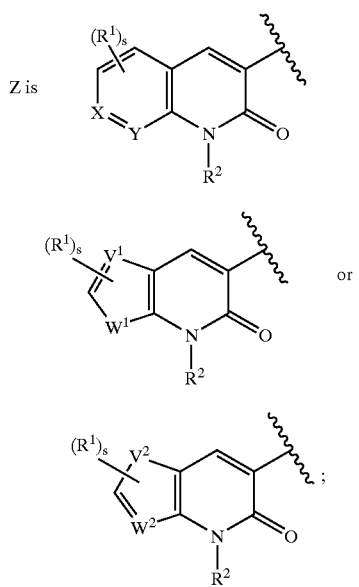

$W^1$ is S, O, or N—R;
$V^1$ is N or C;
$W^2$ is N or C;
$V^2$ is S, O, or N—R;
a is 0 or 1;
b is 0 or 1;
s is 1 or 2;
t is 1, 2, or 3;
X=Y is C=N, N=C, or C=C;
R is H or $C_1$–$C_6$ alkyl;
$R^1$ is selected from:
 1) H,
 2) $(C=O)_aO_bC_1$–$C_{10}$ alkyl,
 3) $(C=O)_aO_b$aryl,
 4) $(C=O)_aO_bC_2$–$C_{10}$ alkenyl,
 5) $(C=O)_aO_bC_2$–$C_{10}$ alkynyl,
 6) $CO_2H$,
 7) halo,
 8) OH,
 9) $O_bC_1$–$C_6$ perfluoroalkyl,
 10) $(C=O)_aNR^7R^8$,
 11) CN,
 12) $(C=O)_aO_bC_3$–$C_8$ cycloalkyl, and
 13) $(C=O)_aO_b$heterocyclyl,
said alkyl, aryl, alkenyl, alkynyl, cycloalkyl, and heterocyclyl is optionally substituted with one or more substituents selected from $R^6$;
$R^2$ and $R^3$ are independently selected from:
 1) H,
 2) $(C=O)O_aC_1$–$C_6$ alkyl,
 3) $(C=O)O_a$aryl,
 4) $C_1$–$C_6$ alkyl,
 5) $SO_2R^a$, and
 6) aryl;
$R^4$ is selected from:
 1) H, provided that Z is not IIA when X=Y is C=C,
 2) $(C=O)_aO_bC_1$–$C_{10}$ alkyl,
 3) $(C=O)_aO_b$aryl,
 4) $(C=O)_aO_bC_2$–$C_{10}$ alkenyl,
 5) $(C=O)_aO_bC_2$–$C_{10}$ alkynyl,
 6) $CO_2H$,
 7) halo,
 8) OH,
 9) $O_bC_1$–$C_6$ perfluoroalkyl,
 10) $(C=O)_aNR^7R^8$,
 11) CN,
 12) $(C=O)_aO_bC_3$–$C_8$ cycloalkyl, and
 13) $(C=O)_aO_b$heterocyclyl,
said alkyl, aryl, alkenyl, alkynyl, cycloalkyl, and heterocyclyl is optionally substituted with one or more substituents selected from $R^6$;
$R^6$ is:
 1) $(C=O)_aO_bC_1$–$C_{10}$ alkyl,
 2) $(C=O)_aO_b$aryl,
 3) $C_2$–$C_{10}$ alkenyl,
 4) $C_2$–$C_{10}$ alkynyl,
 5) $(C=O)_aO_b$ heterocyclyl,
 6) $CO_2H$,
 7) halo,
 8) CN,
 9) OH,
 10) $O_bC_1$–$C_6$ perfluoroalkyl,
 11) $O_a(C=O)_bNR^7R^8$,
 12) oxo,
 13) CHO,
 14) $(N=O)R^7R^8$, and
 15) $(C=O)_aO_bC_3$–$C_8$ cycloalkyl,
said alkyl, aryl, alkenyl, alkynyl, heterocyclyl, and cycloalkyl optionally substituted with one or more substituents selected from $R^{6a}$;
$R^{6a}$ is selected from:
 1) $(C=O)_rO_s(C_1$–$C_{10})$alkyl, wherein r and s are independently 0 or 1,
 2) $O_r(C_1$–$C_3)$perfluoroalkyl, wherein r is 0 or 1,
 3) $(CO_0$–$C_6)$alkylene-$S(O)_mR^a$, wherein m is 0, 1, or 2,
 4) oxo,
 5) OH,
 6) halo,
 7) CN,
 8) $(C_2$–$C_{10})$alkenyl,
 9) $(C_2$–$C_{10})$alkynyl,
 10) $(C_3$–$C_6)$cycloalkyl,
 11) $(C_0$–$C_6)$alkylene-aryl,
 12) $(C_0$–$C_6)$alkylene-heterocyclyl,
 13) $(C_0$–$C_6)$alkylene-$N(R^b)_2$,
 14) $C(O)R^a$,
 15) $(C_0$–$C_6)$alkylene-$CO_2R^a$,
 16) $C(O)H$, and 17) $(C_0$–$C_6)$alkylene-$CO_2H$,
said alkyl, alkenyl, alkynyl, cycloalkyl, aryl, and heterocyclyl is optionally substituted with up to three substituents selected from $R^b$, OH, $(C_1$–$C_6)$alkoxy, halogen, $CO_2H$, CN, $O(C=O)C_1$–$C_6$ alkyl, oxo, and $N(R^b)_2$;

R⁷ and R⁸ are independently selected from:
1) H,
2) (C=O)O$_b$C$_1$–C$_{10}$ alkyl,
3) (C=O)O$_b$C$_3$–C$_8$ cycloalkyl,
4) (C=O)O$_b$aryl,
5) (C=O)O$_b$heterocyclyl,
6) C$_1$–C$_{10}$ alkyl,
7) aryl,
8) C$_2$–C$_{10}$ alkenyl,
9) C$_2$–C$_{10}$ alkynyl,
10) heterocyclyl,
11) C$_3$–C$_8$ cycloalkyl,
12) SO$_2$R$^a$, and
13) (C=O)NRb2,
said alkyl, cycloalkyl, aryl, heterocylyl, alkenyl, and alkynyl is optionally substituted with one or more substituents selected from R$^{6a}$, or
R⁷ and R⁸ can be taken together with the nitrogen to which they are attached to form a monocyclic or bicyclic heterocycle with 5–7 members in each ring and optionally containing, in addition to the nitrogen, one or two additional heteroatoms selected from N, O and S, said monocylcic or bicyclic heterocycle optionally substituted with one or more substituents selected from R$^{6a}$;
R$^a$ is (C$_1$–C$_6$)alkyl, (C$_3$–C$_6$)cycloalkyl, aryl, or heterocyclyl; and
R$^b$ is H, (C$_1$–C$_6$)alkyl, aryl, heterocyclyl, (C$_3$–C$_6$) cycloalkyl, (C=O)OC$_1$–C$_6$ alkyl, (C=O)C$_1$–C$_6$ alkyl or S(O)$_2$R$^a$.

2. The compound of claim 1, wherein W¹ is S or N—R and V² is S or N—R.

3. The compound of claim 2, wherein
R¹ is selected from:
1) H,
2) (C=O)$_a$O$_b$C$_1$–C$_6$ alkyl,
3) (C=O)$_a$O$_b$C$_2$–C$_6$ alkenyl,
4) (C=O)$_a$O$_b$C$_2$–C$_6$ alkynyl,
5) CO$_2$H,
6) halo,
7) OH,
8) O$_b$C$_1$–C$_3$ perfluoroalkyl,
9) CN, and
10) (C=O)$_a$O$_b$C$_3$–C$_6$ cycloalkyl;
R² and R³ are independently selected from:
1) H,
2) (C=O)O$_a$C$_1$–C$_6$ alkyl,
3) C$_1$–C$_6$ alkyl, and
4) SO$_2$R$^a$;
R⁴ is selected from:
1) H, provided that Z is not IIA when X=Y is C=C,
2) (C=O)$_a$O$_b$C$_1$–C$_6$ alkyl,
3) (C=O)$_a$O$_b$aryl,
4) (C=O)$_a$O$_b$C$_2$–C$_6$ alkenyl,
5) (C=O)$_a$O$_b$C$_2$–C$_6$ alkynyl,
6) CO$_2$H,
7) halo,
8) OH,
9) O$_b$C$_1$–C$_3$ perfluoroalkyl,
10) (C=O)$_a$NR⁷R⁸,
11) CN,
12) (C=O)$_a$O$_b$C$_3$–C$_6$ cycloalkyl, and
13) (C=O)$_a$O$_b$heterocyclyl,
said alkyl, aryl, alkenyl, alkynyl, cycloalkyl, and heterocyclyl is optionally substituted with one or more substituents selected from R⁶;

R⁶ is:
1) (C=O)$_a$O$_b$C$_1$–C$_6$ alkyl,
2) (C=O)$_a$O$_b$aryl,
3) C$_2$–C$_6$ alkenyl,
4) C$_2$–C$_6$ alkynyl,
5) (C=O)$_a$O$_b$ heterocyclyl,
6) CO$_2$H,
7) halo,
8) CN,
9) OH,
10) O$_b$C$_1$–C$_3$ perfluoroalkyl,
11) O$_a$(C=O)$_b$NR⁷R⁸,
12) oxo,
13) CHO,
14) (N=O)R⁷R⁸, and
15) (C=O)$_a$O$_b$C$_3$–C$_6$ cycloalkyl,
said alkyl, aryl, alkenyl, alkynyl, heterocyclyl, and cycloalkyl optionally substituted with one or more substituents seicted from R$^{6a}$;
R$^{6a}$ is selected from:
1) (C=O)$_r$O$_s$(C$_1$–C$_6$)alkyl, wherein r and s are independently 0 or 1,
2) O$_r$(C$_1$–C$_3$)perfluoroalkyl, wherein r is 0 or 1,
3) (C$_0$–C$_6$)alkylene-S(O)$_m$R$^a$, wherein m is 0, 1, or 2,
4) oxo,
5) OH,
6) halo,
7) CN,
8) (C$_2$–C$_{10}$)alkenyl,
9) (C$_2$–C$_{10}$)alkynyl,
10) (C$_3$–C$_6$)cycloalkyl,
11) (C$_0$–C$_6$)alkylene-aryl,
12) (C$_0$–C$_6$)alkylene-heterocyclyl,
13) (C$_0$–C$_6$)alkylene-N(R$^b$)$_2$,
14) C(O)R$^a$,
15) (C$_0$–C$_6$)alkylene-CO$_2$R$^a$,
16) C(O)H, and
17) (C$_0$–C$_6$)alkylene-CO$_2$H,
said alkyl, alkenyl, alkynyl, cycloalkyl, aryl, and heterocyclyl is optionally substituted with up to three substituents selected from R$^b$, OH, (C$_1$–C$_6$)alkoxy, halogen, CO$_2$H, CN, O(C=O)C$_1$–C$_6$ alkyl, oxo, and N(R$^b$)$_2$;
R⁷ and R⁸ are independently selected from:
1) H,
2) (C=O)O$_b$C$_1$–C$_6$ alkyl,
3) (C=O)O$_b$C$_3$–C$_6$ cycloalkyl,
4) (C=O)O$_b$aryl,
5) (C=O)O$_b$heterocyclyl,
6) C$_1$–C$_6$ alkyl,
7) aryl,
8) C$_2$–C$_6$ alkenyl,
9) C$_2$–C$_6$ alkynyl,
10) heterocyclyl,
11) C$_3$–C$_6$ cycloalkyl,
12) SO$_2$R$^a$, and
13) (C=O)NR$^b$$_2$,
said alkyl, cycloalkyl, aryl, heterocylyl, alkenyl, and alkynyl is optionally substituted with one or more substituents selected from R$^{6a}$, or
R⁷ and R⁸ can be taken together with the nitrogen to which they are attached to form a monocyclic, 5–7 membered heterocycle and optionally containing, in addition to the nitrogen, one additional heteroatom selected from N, O and S, said heterocycle optionally substituted with one or more substituents selected from R$^{6a}$.

4. The compound of claim 1, wherein

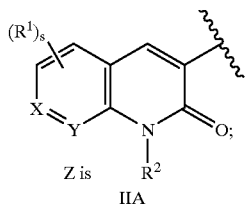

IIA $X=Y$ is $C=C$;
R is H or $C_1-C_6$ alkyl;
$R^1$ is selected from:
1) H,
2) $(C=O)_aO_bC_1-C_6$ alkyl,
3) $(C=O)_aO_bC_2-C_6$ alkenyl,
4) $(C=O)_aO_bC_2-C_6$ alkynyl,
5) $CO_2H$,
6) halo,
7) OH,
8) $O_bC_1-C_3$ perfluoroalkyl,
9) CN, and
10) $(C=O)_aO_bC_3-C_8$ cycloalkyl;
$R^2$ and $R^3$ are independently selected from:
1) H,
2) $(C=O)O_aC_1-C_6$ alkyl,
3) $C_1-C_6$ alkyl, and
4) $SO_2R^a$;
$R^4$ is selected from:
1) $(C=O)_aO_bC_1-C_{10}$ alkyl,
2) $(C=O)_aO_b$aryl,
3) $(C=O)_aO_bC_2-C_{10}$ alkenyl,
4) $(C=O)_aO_bC_2-C_{10}$ alkynyl,
5) $CO_2H$,
6) halo,
7) OH,
8) $O_bC_1-C_6$ perfluoroalkyl,
9) $(C=O)_aNR^7R^8$,
10) CN,
11) $(C=O)_aO_bC_3-C_8$ cycloalkyl, and
12) $(C=O)_aO_b$heterocyclyl,
said alkyl, aryl, alkenyl, alkynyl, cycloalkyl, and heterocyclyl is optionally substituted with one or more substituents selected from $R^6$;
$R^7$ and $R^8$ are independently selected from:
1) H,
2) $(C=O)O_bC_1-C_{10}$ alkyl,
3) $(C=O)O_bC_3-C_8$ cycloalkyl,
4) $(C=O)O_b$aryl,
5) $(C=O)O_b$heterocyclyl,
6) $C_1-C_{10}$ alkyl,
7) aryl,
8) $C_2-C_{10}$ alkenyl,
9) $C_2-C_{10}$ alkynyl,
10) heterocyclyl,
11) $C_3-C_8$ cycloalkyl,
12) $SO_2R^a$, and
13) $(C=O)NR^b_2$,
said alkyl, cycloalkyl, aryl, heterocylyl, alkenyl, and alkynyl is optionally substituted with one or more substituents selected from $R^{6a}$, or
$R^7$ and $R^8$ can be taken together with the nitrogen to which they are attached to form a monocyclic 5–7 memebered heterocycle and optionally containing, in addition to the nitrogen, one additional heteroatom selected from N, O and S, said heterocycle optionally substituted with one or more substituents selected from $R^{6a}$.

5. The compound of claim 4, wherein
s is 1;
t is 1 or 2;
R is H or $C_1-C_6$ alkyl;
$R^1$ is selected from:
1) H,
2) $OC_1-C_6$ alkyl,
3) $C_1-C_6$ alkyl,
4) halo,
5) OH,
6) $OC_1-C_3$ perfluoroalkyl,
7) $OC_1-C_3$ perfluoroalkyl,
8) $OC_3-C_6$ cycloalkyl, and
9) $C_3-C_6$ cycloalkyl;
$R^2$ and $R^3$ are H;
$R^4$ is selected from:
1) $OC_1-C_6$ alkyleneNR$^7$R$^8$,
2) $(C=O)_aC_0-C_6$ alkyl, said alkyl optionally substituted with OH, $CO_2H$, or $OC_1-C_6$ alkyl,
3) $OC_0-C_6$ alkylene-heterocyclyl, optionally substituted with one to three substituents selected from $R^{6a}$,
4) $C_0-C_6$ alkyleneNR$^7$R$^8$,
5) $(C=O)NR^7R^8$, and
6) $OC_1-C_3$ alkylene-$(C=O)NR^7R^8$.

6. A compound selected from:
3-[5-(2-piperidin-1-yl-ethoxy)-benzimidazol-2-yl]-quinolin-2-one;
3-[5-(2-piperidin-1-yl-propoxy)-benzimidazol-2-yl]-quinolin-2-one;
2-(2-oxo-1,2-dihydro-quinolin-3-yl)-benzoimidazole-5-carboxylic acid (2-pyrrolidin-1-yl-ethyl)-amide;
3-[5-(1-piperazinylcarbonyl)-1H-benzimidazol-2-yl]-2(1H)-quinolinone; and
3-{5-[(4-amino-1-piperidinyl)carbonyl]-1H-benzimidazol-2-yl}-2(1H)-quinolinone, or a pharmaceutically acceptable salt or stereoisomer thereof.

7. A pharmaceutical composition which is comprised of a compound in accordance with claim 1 and a pharmaceutically acceptable carrier.

8. A method of treating or preventing cancer in a mammal in need of such treatment which is comprised of administering to said mammal a therapeutically effective amount of a compound of claim 1.

9. A method of treating cancer or preventing cancer in accordance with claim 8 wherein the cancer is selected from cancers of the brain, genitourinary tract, lymphatic system, stomach, larynx and lung.

10. A method of treating or preventing cancer in accordance with claim 8 wherein the cancer is selected from histiocytic lymphoma, lung adenocarcinoma, small cell lung cancers, pancreatic cancer, gioblastomas and breast carcinoma.

11. A method of treating or preventing a disease in which angiogenesis is implicated, which is comprised of administering to a mammal in need of such treatment a therapeutically effective amount of a compound of claim 1.

12. A method in accordance with claim 11 wherein the disease is an ocular disease.

13. A method of treating or preventing retinal vascularization which is comprised of administering to a mammal in need of such treatment a therapeutically effective amount of compound of claim 1.

14. A method of treating or preventing diabetic retinopathy which is comprised of administering to a mammal in need of such treatment a therapeutically effective amount of compound of claim 1.

15. A method of treating or preventing age-related macular degeneration which is comprised of administering to a mammal in need of such treatment a therapeutically effective amount of a compound of claim 1.

16. A method of treating or preventing inflammatory diseases which comprises administering to a mammal in need of such treatment a therapeutically effective amount of a compound of claim 1.

17. A method according to claim 16 wherein the inflammatory disease is selected from rheumatoid arthritis, psoriasis, contact dermatitis and delayed hypersensitivity reactions.

18. A method of treating or preventing a tyrosine kinase-dependent disease or condition which comprises administering a therapeutically effective amount of a compound of claim 1.

19. A pharmaceutical composition made by combining the compound of claim 1 and a pharmaceutically acceptable carrier.

20. A process for making a pharmaceutical composition which comprises combining a compound of claim 1 with a pharmaceutically acceptable carrier.

21. A method of treating or preventing bone associated pathologies selected from osteosarcoma, osteoarthritis, and rickets which comprises administering a therapeutically effective amount of a compound of claim 1.

22. The composition of claim 7 further comprising a second compound selected from:

1) an estrogen receptor modulator,
 2) an androgen receptor modulator,
 3) retinoid receptor modulator,
 4) a cytotoxic agent,
 5) an antiproliferative agent,
 6) a prenyl-protein transferase inhibitor,
 7) an HMG-CoA reductase inhibitor,
 8) an HIV protease inhibitor,
 9) a reverse transcriptase inhibitor, and
 10) another angiogenesis inhibitor.

23. The composition of claim 22, wherein the second compound is another angiogenesis inhibitor selected from the group consisting of a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF.

24. The composition of claim 22, wherein the second compound is an estrogen receptor modulator selected from tamoxifen and raloxifene.

25. A method of treating cancer which comprises administering a therapeutically effective amount of a compound of claim 1 in combination with radiation therapy.

26. A method of treating or preventing cancer which comprises administering a therapeutically effective amount of a compound of claim 1 in combination with a compound selected from:

1) an estrogen receptor modulator,
 2) an androgen receptor modulator,
 3) retinoid receptor modulator,
 4) a cytotoxic agent,
 5) an antiproliferative agent,
 6) a prenyl-protein transferase inhibitor,
 7) an HMG-CoA reductase inhibitor,
 8) an HIV protease inhibitor,
 9) a reverse transcriptase inhibitor, and
 10) another angiogenesis inhibitor.

27. A method of treating cancer which comprises administering a therapeutically effective amount of a compound of claim 1 in combination with radiation therapy and a compound selected from:

1) an estrogen receptor modulator,
 2) an androgen receptor modulator,
 3) retinoid receptor modulator,
 4) a cytotoxic agent,
 5) an antiproliferative agent,
 6) a prenyl-protein transferase inhibitor,
 7) an HMG-CoA reductase inhibitor,
 8) an HIV protease inhibitor,
 9) a reverse transcriptase inhibitor, and
 10) another angiogenesis inhibitor.

28. A method of treating or preventing cancer which comprises administering a therapeutically effective amount of a compound of claim 1 and paclitaxel or trastuzumab.

29. A method of treating or preventing cancer which comprises administering a therapeutically effective amount of a compound of claim 1 and a GPIIb/IIIa antagonist.

30. The method of claim 29 wherein the GPIIb/IIIa antagonist is tirofiban.

31. A method of reducing or preventing tissue damage following a cerebral ischemic event which comprises administering a therapeutically effective amount of a compound of claim 1.

\* \* \* \* \*